United States Patent
Allen et al.

(10) Patent No.: US 6,849,781 B2
(45) Date of Patent: Feb. 1, 2005

(54) STARCH SYNTHASE ISOFORM V

(75) Inventors: Stephen M. Allen, Wilmington, DE (US); Karlene H. Butler, Newark, DE (US); Catherine J. Thorpe, St Albans (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 261 days.

(21) Appl. No.: 10/163,214

(22) Filed: Jun. 5, 2002

(65) Prior Publication Data

US 2003/0097688 A1 May 22, 2003

Related U.S. Application Data

(60) Provisional application No. 60/297,099, filed on Jun. 8, 2001.

(51) Int. Cl.[7] .................. C12N 15/29; C12N 15/82; C12N 5/04; A01H 5/00; C12P 19/04
(52) U.S. Cl. ............. 800/284; 800/278; 800/286; 435/320.1; 435/419; 435/468; 536/23.2; 536/23.6; 536/24.5
(58) Field of Search ................. 800/278, 284, 800/286; 435/320.1, 419, 468; 536/23.2, 23.6

(56) References Cited

U.S. PATENT DOCUMENTS 6,211,436 B1   4/2001   Kossmann et al.

FOREIGN PATENT DOCUMENTS

WO   97/26362   7/1997
WO   01/14540   3/2001

OTHER PUBLICATIONS

National Center for Biotechnology Information General Identifier No. 4582783, Apr. 13, 1999, Starch synthase, isoform V [*Vigna unguiculata*].
National Center for Biotechnology Information General Identifier No. 15717885, Sep. 20, 2001, Starch synthase isoform IV [*Triticum aestivum*].
National Center for Biotechnology Information General Identifier No. 4715636, Apr. 29, 1999.
Anne Edwards et al., Eur. J. Biochem., vol. 266, 724–736, 1999, Specificity of Starch Synthase Isoforms from Potato.

*Primary Examiner*—David T. Fox

(57) ABSTRACT

Isolated nucleic acid fragments encoding starch synthase isoform V. are presented. Recombinant DNA constructs encoding all or a portion of starch synthase isoform V, in sense or antisense orientation, can be made, wherein expression of the recombinant DNA construct results in production of altered levels of the starch synthase isoform V in a transformed host cell.

12 Claims, 5 Drawing Sheets

```
SEQ ID NO:2    *  ***  *** ** *  *   **   *  *    *  **      *  *  **           **
SEQ ID NO:6  1 MSCSAAAGAEATALLF-RSAAPSTIVGR--HRLAMSRRTSRRNLRTGVHPHQKSAPSANH
SEQ ID NO:12 1 MAC-LAAGAEAAPLLFRRRLAPSPVAAR--RRLLVSCRARRRGLRTAAELPRKSTSNDKH
SEQ ID NO:13 1 MACSAAAGVEATALLSPRCPAPSPPDGRSRRRLALASRTRHRSLRAAAQRPHKSATGADP
             1 ------------------------------------------------------------
                                                                           60

SEQ ID NO:2     *   *    *  ** *    * *  ** *** **   ***  ***  *  ******
SEQ ID NO:6  58 --RNRASIQRDRASASIDEEQKQMSEDENGLLDIQLEDLVGMIQNTQKNILLLNQARLQA
SEQ ID NO:12 58 --HNRVNMQRDEASVSSDKERQEKYGDENGISNLQLEDLIQMIQNTEKNIMLLNQARLQA
SEQ ID NO:13 61 LYNNRANVRSDEASVSAEKERQRKYNDGDGISNLKLEDLVGMIQNTEKNILLLNQARLQA
             1 ------------------------MIKNAEKNILLLNQARVHA
            61                                                        120

SEQ ID NO:2     *  ****  **   *  *     *       *
SEQ ID NO:6  116 LERADKILKEKETLQQKINILEMKLSETGKQSVLSSE-----------------------
SEQ ID NO:12 116 LEHVETVLKEKEDLQRKLKILETRLSETDARLKLSAE-----------------------
SEQ ID NO:13 121 MEHADKVLKEKEALQRKINILETRLSETDEQHKLSSE-----------------------
             20 LEDLEKILAEKEALQGEINVLAMRLAESDVRIEVAAQEKTRVELLEGELEKLRSELAQKG
            121                                                        180

SEQ ID NO:2      *     *   **  *   ***
SEQ ID NO:6  153 -------------VKSDEE-------SL--EFDVVKEENMLLKDEMNFLKGKLI
SEQ ID NO:12 153 -------------GQFGTEINDSLP------VL--ELDDIKEENMLLKDDIQFLKTMLI
SEQ ID NO:13 158 -------------GNFS---DSPLA------L--ELGILKEENILLKEDIEFFKTKLI
             80 SIEGRDAELHELQNGVFSDAITNNLSHNDKIHSLTEELNSIREENATLKNAIESFKAQLN
            181                                                        240

FIG. 1A
```

```
                          *      ***    *        *           *      *       ***  *     ***  *
SEQ ID NO:2   185 EITETEESLFKLEKECALLNASLRELECTSTSAQSDVLKLGPLQQD--AWWEKVENLEDL
SEQ ID NO:6   191 EVAETENSIFTLEKERALLDASLRELESRFIDAQADMLKSDPRQYD--AWWEKVENLGDL
SEQ ID NO:12  192 EVAEIEEGIFKLEKEHALLDASLRELESRFIAAQADTMKLGPR--D--AWWEKVEKLEDL
SEQ ID NO:13  140 DVANNDERLAVLEKERLSIRSALKDMESKLSIFPEDVSELSTLRVECKDLSDKVENLQLL
                  241                                                          300

*        *   **     *       ****          **     *
SEQ ID NO:2   243 LDSTANQVEHASLTLDGYRDFQDKVDKLKASLGTTNVSEFCLYLV-----DILQQRVKSVE
SEQ ID NO:6   249 LETATNKVENAAMVLGRNHDLEDKVDKLEASLAEANISKFSCYFV-----DLLQEKIKSVE
SEQ ID NO:12  248 LETTANQVEHAAVILDHNHDLQDRLDNLEASLQAANISKFSCSLV-----DLLQQKVLVE
SEQ ID NO:13  200 LDKATKQDSQAVTVLQQNQDLQRKVDKLEASLEEANIYKLSSDKLQKSNELMQQKIKLLE
                  301                                                          360

*  *      ***       *          *    *  **  *         ****
SEQ ID NO:2   299 ERFQACNHEMHSQIELYEHSIVEFHGTLSKLINESEKKSMEHYAEGMPSEFWSRISLLID
SEQ ID NO:6   305 ERFQVCNHEMHSQIELYENSIAEFHDILSKLVEETEKRSLEHSASSMPSELWSRISLLID
SEQ ID NO:12  304 DRFQACNSEMHSQIELYEHSIVEFHDTLSKLIEESEKRSLENFTGNMPSELWSKISLLID
SEQ ID NO:13  260 SQLQKSDEDINSYVQLYQQSVKEFQDTLDLLKKESKRRAPDEPVEDMPWEFWSRLLLLID
                  361                                                          420

**  ***  *            *          *    ***            *
SEQ ID NO:2   359 GWSLEKKISINDASMLREMAWKRDNRLREAYLSSRGMEERELIDSFLKMALPGTSSGLHI
SEQ ID NO:6   365 GWLLEKRISYNDANTLREMVRKRDSCLREAYLSCRGMKDREIVDNFLKITLPGTSSGLHI
SEQ ID NO:12  364 GWLLEKKISYNDASMLREMVQKRDSRLREAYLSYRGTENREVMDNLLKMALPGTSSGLHI
SEQ ID NO:13  320 GWALEKKISVDDAKLLREKVWKRDKSVSDVYMAYKEKTEHEAISAFLGLTSSATSPGLYV
                  421                                                          480

FIG. 1B
```

```
                      *****************************  ******  *    *                     ***
SEQ ID NO:2    419 VHIAAEMAPVAKVGGLADVISGLGKALQKKGHLVEIILPKYDCMQHNQINNLKVLDVVVK
SEQ ID NO:6    425 IHIAAEMAPVAKVGGLADVISGLGKALQKKGHLVEIILPKYDCMQNDQVNNLKVLDVVVQ
SEQ ID NO:12   424 AHIAAEMAPVAKVGGLADVISGLGKALQKKGHLVEIILPKYDCMQVDQVSNLKVLDVLVQ
SEQ ID NO:13   380 IHIAAEMAPVAKVGGLGDVISGLSKALQKKGHLVEIILPKYDCMQYDRIGDLRALDVVIE
                   481                                                           540

*** *  *****    ** *****************   ** *  **** *****  *****
SEQ ID NO:2    479 SYFEGNMFANKIWTGTVEGLPVYFIEPQHPGKFFWRAQYYGEHDDFKRFSYFSRVALELL
SEQ ID NO:6    485 SYFEGNLFNNKIWTGTVEGLPVYFIEPQHPAKFFWRAQYYGEHDDFKRFAYFSRAALELL
SEQ ID NO:12   484 SYFEGNMFNNKIWTGTVEGLPVYFIEPQHPAMFFSRAQYYGEHDDFKRFSYFSRAALELL
SEQ ID NO:13   440 SYFDGQLFKNKIWGTVEGLPVYFIEPHHPGKFFWRGDYYGAHDDFRRFSYFSRAALEFL
                   541                                                           600

*  ****************************   **  *************** ** **
SEQ ID NO:2    539 YQSGKKVDIIHCHDWQTAFVAPLYWDVYANLGFNSARICFTCHNFEYQGIAPAQDLAYCG
SEQ ID NO:6    545 YQSQKKIDIIHCHDWQTAFVAPLYWEAYANLGFNSARICFTCHNFEYQGAAPAQDLACCG
SEQ ID NO:12   544 YQSGKKVDIIHCHDWQTAFVAPLYWDVYANLGFNSARICFTCHNFEYQGTAPARDLAWCG
SEQ ID NO:13   500 LQAGKKPDIIHCHDWQTAFIAPLYWDVYAPKGLNSARICFTCHNFEYQGTAGASELEACG
                   601                                                           660

**  ***      ***   *                 ************** ****** **  *
SEQ ID NO:2    599 LDVDHLDRPDRMRDNS-HGRINVVKGAVVYSNIVTTVSPTYAQEVRS-EGGRGLQDTLKV
SEQ ID NO:6    605 LDVQQLDREDRMRDNS-HGRINVVKGAIVYSNIVTTVSPTYALEVRS-EGGRGLQDSLKL
SEQ ID NO:12   604 LDVEHLDRPDRMRDNS-HGRINAVKGAVVYSNIVTTVSPTYALEVRS-EGGRGLQDTLKV
SEQ ID NO:13   560 LDSHQLNRPDRMQDNSAHNRVNSVKGAVVYSNIVTTVSPTYAQEVRTAEGGKGLHSTLST
                   661                                                           720
```

FIG. 1C

```
SEQ ID NO:2    657  HSKKFVGILNGIDTDTWNPSTDRFLKVQYSANDLYGKSANKAALRKQLKLASTQASQPLV
SEQ ID NO:6    663  HSRKFVGILNGIDTDTWNPSTDRHLKVQYNANDLQGKAANKAALRKQLNLSSTNASQPLV
SEQ ID NO:12   662  HSRKFLGILNGIDTDTWNPCTDRYLKVQYNAKDLQGKAANKAALREQLNLASAYPSQPLV
SEQ ID NO:13   620  HSKKFIGILNGIDTDIWNPATDPFLQVQYNANDLQGKSENKEALRRNLGLSSADVRRPLV
                                                                                 780

SEQ ID NO:2    717  GCITRLVPQKGVHLIRHAIYKITELGGQFVLLGSSPVQHIQREFEGIADQFQNNNNVRLL
SEQ ID NO:6    723  GCITRLVPQKGVHLIRHAIYKTAELGGQFVLLGSSPVPHIQREFEGIADHFQNNNNIRLL
SEQ ID NO:12   722  GCITRLVAQKGVHLIRHAIYKTAELGGQFVLLGSSPVPEIQREFEGIADHFQNNNNIRLI
SEQ ID NO:13   680  GCITRLVPQKGVHLIRHAIYLTLELGGQFVLLGSSPVPHIQREFEGIANHFQNHDHIRLI
                                                                                 840

SEQ ID NO:2    777  LKYDDALAHMIFAASDMFIVPSMFEPCGLTQMVAMRYGSVPVVRRTGGLNDSVFDLDDET
SEQ ID NO:6    783  LKYDDSLSHWIYAASDMFIVPSMFEPCGLTQMIAMRYGSVPIVRKTGGLNDSVFDFDDET
SEQ ID NO:12   782  LKYDDALSHCIYAASDMFIVPSIFEPCGLTQMIAMRYGSVPIVRKTGGLNDSVFDFDDET
SEQ ID NO:13   740  LKYDESLSHAIYAASDMFIIPSIFEPCGLTQMISMRYGAIPIARKTGGLNDSVFDVDDDT
                                                                                 900

SEQ ID NO:2    837  IPMEVRNGFTFLKADEQDFGNALERAFNYYHRKPEVWKQLVQKDMKIDFSWDTSVSQYEE
SEQ ID NO:6    843  IPKELRNGFTFVHPDEKALSGAMERAFNYYNRKPEVWKQLVQKDMRIDFSWASSASQYED
SEQ ID NO:12   842  IPMEVRNGFTFVKADEQGLSSAMERAFNCYTRKPEVWKQLVQKDMTIDFSWDTSASQYED
SEQ ID NO:13   800  IPSQFRNGFTFLNADEKGINDALVRAINLFTNDPKSWKQLVQKDMNIDFSWDSSAAQYEE
                                                                                 960
```

FIG. 1D

```
SEQ ID NO:2   897 IYQKTATRARAA--A 909
SEQ ID NO:6   903 IYQRAVARARAA--A 915
SEQ ID NO:12  902 IYQKAVARARAV--A 914
SEQ ID NO:13  860 LYSKSVTRGRATKRA 874
                  961         975
```

FIG. 1E

STARCH SYNTHASE ISOFORM V

This application claims the benefit of U.S. Provisional Application No. 60/297,099, filed Jun. 8, 2001, the entire content of which is herein incorporated by reference.

FIELD OF INVENTION

The field of invention relates to plant molecular biology, and more specifically, to nucleic acid fragments encoding starch synthase isoform V proteins in plants and seeds.

BACKGROUND OF INVENTION

The molecular structure of plant starch depends on the degree of polymerization and branching of the component polyglucan chains. Starch granules consist mainly of two different kinds of polymer structures: amylose which primarily consists of unbranched chains of about 1000 glucose molecules, and amylopectin which is much larger than amylose and branches every 20–25 glucose residues. Some starch granules also contain phytoglycogen, a highly branched starch.

A principal enzyme that determines the extent to which these different starch forms are present in a particular starch granule is starch synthase which is involved in elongating the polyglucan chains of starch, transferring the glucose residue from ADP-glucose to the hydroxyl group in the 4-position of the terminal glucose molecule in the polymer. Starch synthases from different plant sources have different catalytic properties (e.g., rate of chain elongation, affinity for different substrates), in part accounting for the differing fine structure of starch granules observed from plant to plant, and even from one developmental stage to another for a given plant.

Expectedly, starch synthase has been the focus of a number of studies. Starch synthase is localized in the plastid, where starch formation in plants occurs. Starch synthase activity has been observed bound to the starch granule ("granule-bound form") or in the supernatant of crude extracts ("soluble form"). The number of isoforms and their expression patterns vary with the plant species and the developmental stage. For example, in maize endosperm, there are at least four starch synthase isoforms, two soluble and at least two granule-bound. In potato tuber, three soluble starch synthase isoforms and at least two granule-bound isoforms have been identified. One of the three soluble isoforms in potato tuber, SSI, is expressed more in leaves than in tubers.

The Waxy locus encodes a granule-bound starch synthase responsible for amylose synthesis and has been cloned from several plant species. Genes encoding different isoforms of soluble starch synthases have been isolated as well. Certain starch synthases remain uncharacterized in detail and it is believed that additional isoforms have yet to be discovered. The chemical properties of a particular starch is ultimately determined by its structure, so that manipulation of starch structure at the molecular level, by modulating the activity of enzymes like starch synthase involved in starch biosynthesis provides a tool for designing starch to suit a particular need, or for obtaining starch of uniform composition. For example, sorghum waxy mutants contain amylopectin exclusively, and their glutinous grains produce wine with higher quality and specific fragrance compared with those of wild-type. Accordingly, genes encoding novel isoforms of starch synthase may prove useful in producing starch structures with novel chemical properties. Disclosed herein are nucleic acid fragments encoding starch synthase including starch synthase isoform V isolated from leaf and young seedling tissue which if expressed in storage organs like seeds or tubers may lead to altered reserve starch composition. Sequence for a starch synthase isoform V from *Vigna unguiculata* (NCBI General Identification No. 4582783) as well as a closely related maize sequence for a partial starch synthase protein (PCT WO 97/26362; U.S. Pat. No. 6,211,436) have been disclosed previously.

SUMMARY OF INVENTION

The present invention includes isolated polynucleotides comprising a nucleotide sequence encoding a polypeptide having starch synthase activity wherein the amino acid sequence of the polypeptide and the amino acid sequence of SEQ ID NO:6 or SEQ ID NO:12 have at least 85% sequence identity. It is preferred that the identity be at least 90%, it is more preferred that the identity be at least 95%. More preferably, the present invention includes isolated polynucleotides encoding the polypeptide sequence of SEQ ID NO:2, SEQ ID NO:6 or SEQ ID NO:12 or nucleotide sequences comprising the nucleotide sequence of SEQ ID NO:1, SEQ ID NO:5 or SEQ ID NO:11. The present invention also includes isolated polynucleotides comprising the complement of nucleotide sequences of the present invention.

The present invention also includes:

in a preferred first embodiment, an isolated polynucleotide comprising: (a) a first nucleotide sequence encoding a first polypeptide comprising at least 740 amino acids, wherein the amino acid sequence of the first polypeptide and the amino acid sequence of SEQ ID NO:6 or SEQ ID NO:12 have at least 85%, 90%, or 95% identity, (b) a second nucleotide sequence encoding a second polypeptide, wherein the amino acid sequence of the second polypeptide comprises the amino acid sequence of SEQ ID NO:2, or (c) the complement of the nucleotide sequence of (a) or (b); the first polypeptide preferably comprises the amino acid sequence of SEQ ID NO:6 or SEQ ID NO:12; the first nucleotide sequence preferably comprises the nucleotide sequence of SEQ ID NO:5 or SEQ ID NO:11 and the second nucleotide sequence preferably comprises the nucleotide sequence of SEQ ID NO:1; the polypeptide preferably has starch synthase activity;

in a preferred second embodiment, a recombinant DNA construct comprising any of the isolated polynucleotides of the present invention operably linked to at least one regulatory sequence, and a cell, a plant, and a seed comprising the recombinant DNA construct;

in a preferred third embodiment, a vector comprising any of the isolated polynucleotides of the present invention;

in a preferred fourth embodiment, an isolated polynucleotide comprising a nucleotide sequence comprised by any of the polynucleotides of the first embodiment, wherein the nucleotide sequence contains at least 30, 40, or 60 nucleotides;

in a preferred fifth embodiment, a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium;

in a preferred sixth embodiment, a method for producing a transgenic plant comprising transforming a plant cell with any of the isolated polynucleotides of the present invention and regenerating a plant from the transformed plant cell, a transgenic plant produced by this method, and seed obtained from this transgenic plant;

in a preferred seventh embodiment, starch obtainable from the transgenic plant or seed of the transgenic plant;

in a preferred eighth embodiment, an isolated polypeptide comprising: (a) a first amino acid sequence, wherein the first amino acid sequence and the amino acid sequence of SEQ ID NO:6 or SEQ ID NO:12 have at least 85%, 90%, or 95% sequence identity, or (b) a second amino acid sequence comprising the amino acid sequence of SEQ ID NO:2; the first amino acid sequence preferably comprises the amino acid sequence of SEQ ID NO:6 or SEQ ID NO:12; the polypeptide preferably has starch synthase activity; the first amino acid sequence preferably comprises at least 740 amino acids;

in a preferred ninth embodiment, a method for isolating a polypeptide encoded by a polynucleotide of the present invention comprising isolating the polypeptide from a cell or culture medium of the cell, wherein the cell comprises a recombinant DNA construct comprising the polynucleotide operably linked to at least one regulatory sequence;

in a preferred tenth embodiment, a virus, preferably a baculovirus, comprising any of the isolated polynucleotides of the present invention or any of the recombinant DNA constructs of the present invention;

in a preferred eleventh embodiment, a method of selecting an isolated polynucleotide that affects the level of expression of a gene encoding a starch synthase isoform V protein or activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of starch synthase isoform V protein or activity in the host cell containing the isolated polynucleotide or the isolated recombinant DNA construct; and (d) comparing the level of starch synthase isoform V protein or activity in the host cell containing the isolated polynucleotide or the isolated recombinant DNA construct with the level of starch synthase isoform V protein or activity in the host cell that does not contain the isolated polynucleotide or the isolated recombinant DNA construct;

in a preferred twelfth embodiment, a method of obtaining a nucleic acid fragment encoding a substantial portion of a starch synthase isoform V protein, preferably a plant starch synthase isoform V protein comprising the steps of: synthesizing an oligonucleotide primer comprising a nucleotide sequence of at least 30 (preferably at least 40, most preferably at least 60) contiguous nucleotides derived from a nucleotide sequence of SEQ ID NOs:1, 3, 5, 7, 9 or 11 and the complement of such nucleotide sequences; and amplifying a nucleic acid fragment (preferably a cDNA inserted in a cloning vector) using the oligonucleotide primer. The amplified nucleic acid fragment preferably will encode a substantial portion of a starch synthase isoform V protein amino acid sequence;

in a preferred thirteenth embodiment, a method of obtaining a nucleic acid fragment encoding all or a substantial portion of the amino acid sequence encoding a starch synthase isoform V protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone;

in a preferred fourteenth embodiment, a method for positive selection of a transformed cell comprising: (a) transforming a host cell with a recombinant DNA construct of the present invention or an expression cassette of the present invention; and (b) growing the transformed host cell, preferably a plant cell, such as a monocot or a dicot, under conditions which allow expression of the starch synthase isoform V polynucleotide in an amount sufficient to complement a null mutant to provide a positive selection means; and in a preferred fifteenth embodiment, a method of altering the level of expression of a starch synthase isoform V protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the starch synthase isoform V protein in the transformed host cell.

BRIEF DESCRIPTION OF THE DRAWINGS
AND SEQUENCE LISTINGS

The invention can be more fully understood from the following detailed description and the accompanying drawings and Sequence Listing which form a part of this application.

FIGS. 1A, 1B, 1C, 1D and 1E show an alignment of the amino acid sequences of starch synthase isoform V encoded by the nucleotide sequences derived from PCR products and corn clone p0070.cwlah82r (SEQ ID NO:2), PCR products and rice clone rls2.pk0001.h8 (SEQ ID NO:6), PCR products and wheat clone wlk8.pk0017.g4 (SEQ ID NO:12), and the starch synthase isoform V from *Vigna unguiculata* (NCBI GI No. 4582783; SEQ ID NO:13). Amino acids which are conserved among all and at least two sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more EST, FIS or PCR sequences ("Contig"), or sequences encoding the entire or functional protein derived from an FIS or a contig ("CGS"). Nucleotide SEQ ID NOs:3, 7, and 9 correspond to nucleotide SEQ ID NOs:1, 3, and 5, respectively, presented in WO 01/14540, published Mar. 1, 2001. Amino acid SEQ ID NOs:4, 8, and 10 correspond to amino acid SEQ ID NOs:2, 4, and 6, respectively, presented in WO 01/14540, published Mar. 1, 2001. The sequence descriptions and Sequence Listing attached hereto comply with the rules governing nucleotide and/or amino acid sequence disclosures in patent applications as set forth in 37 C.F.R. §1.821–1.825.

TABLE 1

Starch Synthase Isoform V

| Protein (Plant Source) | Clone Designation | Status | SEQ ID NO: (Nucleotide) | SEQ ID NO: (Amino Acid) |
| --- | --- | --- | --- | --- |
| Starch Synthase Isoform V (Corn) | p0070.cw1ah82r (FIS and PCR) | CGS | 1 | 2 |
| Starch Synthase Isoform V (Rice) | rls2.pk0001.h8 | EST | 3 | 4 |
| Starch Synthase Isoform V (Rice) | rls2.pk0001.h8 (FIS and PCR) | CGS | 5 | 6 |
| Starch Synthase Isoform V (Soybean) | sl2.pk133.c1 | EST | 7 | 8 |
| Starch Synthase Isoform V (Wheat) | wlk8.pk0017.g4 | FIS | 9 | 10 |
| Starch Synthase Isoform V (Wheat) | wlk8.pk0017.g4 (FIS and PCR) | CGS | 11 | 12 |

SEQ ID NO:13 corresponds to the starch synthase isoform V from *Vigna unguiculata* (NCBI GI No. 4582783).

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF PREFERRED EMBODIMENTS

The problem to be solved was to identify polynucleotides that encode novel starch synthase proteins, such as starch synthase isoform V. These polynucleotides may be used in plant cells to alter the starch biosynthesis pathway. More specifically, the polynucleotides of the instant invention may be used to create transgenic plants where the starch synthase isoform V levels in certain tissues are altered with respect to non-transgenic plants which would result in plants with a different starch profile in those tissues. Accordingly, the availability of nucleic acid sequences encoding all or a portion of a starch synthase isoform V would facilitate studies to better understand starch biosynthesis. The present invention has solved this problem by providing polynucleotide and deduced polypeptide sequences corresponding to novel starch synthase isoform V proteins from corn (*Zea mays*), rice (*Oryza sativa*), and wheat (*Triticum aestivum*), and a partial starch synthase isoform V protein from soybean (*Glycine max*).

In the context of this disclosure, a number of terms shall be utilized. The term "starch synthase isoform V" refers to a novel starch synthase isolated from *Vigna unguiculata* (NCBI General Identification No. 4582783) as well as closely related sequences from other plants, such as maize (PCT WO 97/26362). Starch synthase isoform V is predicted to be related to the starch synthase group due to the presence of amino acid motifs conserved among the glucosyltransferase family, e.g., the residues that make up two putative ADP/ADP-glucose binding sites. Starch synthase isoform V is most closely related to the Class III starch synthases. Evolutionary sequence conservation suggests that although starch synthase III and starch synthase isoform V are more similar to each other than to the other classes of starch synthases, they should be treated as distinct classes. The wheat homolog of *V. unguiculata* starch synthase isoform V has been called wheat starch synthase isoform IV (NCBI GI No. 15717885).

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NOs:1, 3, 5, 7, 9 or 11, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NO:1, 3, 5, 7, 9 or 11, and the complement of such nucleotide sequences may be used to affect the expression and/or function of a starch synthase isoform V in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 250 amino acids, and most preferably at least 740 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. Sequence alignments and percent identity calculations were performed using the Megalign program of the LASER-GENE bioinformatics computing suite (DNASTAR Inc., Madison, Wis.). Multiple alignment of the sequences was performed using the ClustalV method of alignment (Higgins and Sharp (1989) *CABIOS.* 5:151–153) with the following parameters: GAP PENALTY=9, GAP LENGTH PENALTY=9. The following default parameters for pairwise alignments were used for the ClustalV method: KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also the explanation of the BLAST algorithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15: 1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632). A "mitochondrial signal peptide" is an amino acid sequence which directs a precursor protein into the mitochondria (Zhang and Glaser (2002) *Trends Plant Sci* 7:14–21).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277; Ishida Y. et al. (1996) *Nature Biotech.* 14:745–750) and particle-accelerated or "gene gun" transformation technology (Klein et al. (1987) *Nature (London)* 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

The present invention includes an isolated polynucleotide comprising: (a) a first nucleotide sequence encoding a starch synthase isoform V polypeptide having at least 85% sequence identity, based on the ClustalV method of alignment, when compared to a polypeptide of SEQ ID NO:6 or SEQ ID NO:12, or (b) a second nucleotide sequence encoding a starch synthase isoform V polypeptide comprising the amino acid sequence of SEQ ID NO:2.

This invention also includes the isolated complement of such polynucleotides, wherein the complement and the polynucleotide preferably consist of the same number of nucleotides, and the nucleotide sequences of the complement and the polynucleotide preferably have 100% complementarity.

Nucleic acid fragments encoding at least a portion of several starch synthase isoform V have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other starch synthase isoform V proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NOs:1, 3, 5, 7, 9 or 11 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another preferred embodiment, this invention includes viruses and host cells comprising either the recombinant DNA constructs of the invention as described herein or isolated polynucleotides of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of starch and its composition in those cells.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant isolated polynucleotide(s) (or recombinant DNA construct(s)) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct(s) described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), nuclear localization signals (Raikhel (1992) *Plant Phys.* 100:1627–1632) or mitochondrial signal sequences (Zhang and Glaser (2002) *Trends Plant Sci* 7:14–21) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another preferred embodiment, the present invention includes a starch synthase isoform V polypeptide comprising: (a) a first amino acid sequence comprising at least 740 amino acids, wherein the first amino acid sequence and the amino acid sequence of SEQ ID NO:6 or SEQ ID NO:12 have at least 85%, 90%, or 95% sequence identity based on the ClustalV alignment method, or (b) a second amino acid sequence comprising the amino acid sequence of SEQ ID NO:2. The first amino acid sequence preferably comprises the amino acid sequence of SEQ ID NO:6 or SEQ ID NO:12. The polypeptide preferably has starch synthase activity.

The instant polypeptides (or portions thereof may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded starch synthase isoform V. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several kb to several hundred kb; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries: Isolation and Sequencing of cDNA Clones cDNA libraries representing mRNAs from corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| p0070 | Corn Whorl/Leaf Tissue at V6-V7* following ECB1 (European Corn Borer) Infestation from ECB1 and ECB2 Resistant Line | p0070.cwlah82r |
| rls2 | Susceptible Rice Leaf 15 Days After Germination, 2 Hours After Infection of Strain *Magnaporthe grisea* 4360-R-67 (AVR2-YAMO) | rls2.pk0001.h8 |
| sl2 | Soybean Two-Week-Old Developing Seedling Treated With 2.5 ppm chlorimuron | sl2.pk133.c1 |
| wlk8 | Wheat Seedling 8 Hours After Herbicide Treatment** | wlk8.pk0017.g4 |

*Corn developmental stages are explained in the publication "How a corn plant develops" from the Iowa State University Coop. Ext. Service Special Report No. 48 reprinted June 1993
**Application of 6-iodo-2-propoxy-3-propyl-4(3H)-quinazolinone; synthesis and methods of using this compound are described in USSN 08/545,827, incorporated herein by reference cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding starch synthase isoform V were identified by conducting BLAST (Basic Local Alignment Search Tool; Altschul et al. (1993) *J. Mol. Biol.* 215:403–410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the GenBank database as described above. ESTs that contain sequences more 5- or 3-prime can be found by using the BLASTn algorithm (Altschul et al (1997) Nucleic Acids Res. 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Starch Synthase Isoform V

The BLASTX search using the EST sequences from clones listed in Table 3 revealed similarity of the polypeptides encoded by the cDNAs to starch synthase isoform V from Vigna unguiculata (NCBI GenBank Identifier (GI) No. 4582783; SEQ ID NO:13). Shown in Table 3 are the BLAST results for individual ESTs ("EST"), the sequences of the entire cDNA inserts comprising the indicated cDNA clones ("FIS"), the sequences of contigs assembled from two or more EST, FIS or PCR sequences ("Contig"), or sequences encoding an entire protein derived from an FIS or a contig ("CGS"):

TABLE 3

BLAST Results for Sequences Encoding Polypeptides Homologous to Starch Synthase Isoform V

| Clone | Status | BLAST pLog Score 4582783 |
| --- | --- | --- |
| rls2.pk0001.h8 | EST | 46.30 |
| sl2.pk133.cl | EST | 10.50 |
| wlk8.pk0017.g4 | FIS | 128.00 |

Amino acid sequences derived from nucleotide sequences obtained from clones rls2.pk0001.h8 (SEQ ID NO:4) and wlk8.pk0017.g4 (SEQ ID NO:10) displayed higher pLog scores—64.22 and 144.00, respectively—with a partial starch synthase protein from maize disclosed in PCT WO 97/26362 and U.S. Pat. No. 6,211,436. This maize sequence is 60.4% identical at the amino acid level with the sequence of starch synthase isoform V from Vigna unguiculata (NCBI GI No. 4582783; SEQ ID NO:13), making it likely to encode a maize starch synthase isoform V.

Sequence alignments and BLAST scores and probabilities indicate that the nucleic acid fragments comprising the instant cDNA clones encode a substantial portion of a starch synthase isoform V. These sequences represent the first rice, soybean, and wheat sequences that have been indicated to encode starch synthase isoform V. A public rice EST sequence (NCBI General Identification No. 4715636) is shown by BLAST analysis to have 91 % identity at the nucleotide level over 29% of the sequence disclosed herein that was derived from clone rls2.pk0001.h8 (SEQ ID NO:3); this public sequence however has not been characterized as encoding starch synthase isoform V.

The sequence of the entire cDNA insert in the clones listed in Table 3 was determined. Further sequencing and searching of the DuPont proprietary database allowed the identification of other clones encoding starch synthase isoform V. Full-length insert sequencing of clones p0070.cwlah82r, rls2.pk0001.h8, and wlk8.pk0017.g4 indicated that the entire cDNA inserts in said clones lacked the coding sequence for the N-terminal portion of starch synthase isoform V. To obtain the lacking sequence, PCR-based methods well known in the art were employed. The BLASTX search using the EST sequences from clones listed in Table 4 revealed similarity of the polypeptides encoded by the cDNAs to starch synthase isoform V from Vigna unguiculata (NCBI GI No. 4582783; SEQ ID NO:13). Shown in Table 4 are the BLAST results for individual ESTs ("EST"), the sequences of the entire cDNA inserts comprising the indicated cDNA clones ("FIS"), the sequences of contigs assembled from two or more EST, FIS or PCR sequences ("Contig"), or sequences encoding an entire or functional protein derived from an FIS or a contig ("CGS"):

TABLE 4

BLAST Results for Sequences Encoding Polypeptides Homologous to Starch Synthase Isoform V

| Clone | Status | BLAST pLog Score NCBI GI No. 4582783 |
| --- | --- | --- |
| p0070.cwlah82r (FIS and PCR) | CGS | >180.00 |
| rls2.pk0001.h8 (FIS and PCR) | CGS | >180.00 |

TABLE 4-continued

BLAST Results for Sequences Encoding Polypeptides Homologous to Starch Synthase Isoform V

| Clone | Status | BLAST pLog Score NCBI GI No. 4582783 |
|---|---|---|
| wlk8.pk0017.g4 (FIS and PCR) | CGS | >180.00 |

FIG. 1 presents an alignment of the amino acid sequences set forth in SEQ ID NOs:2, 6 and 12 and the *Vigna unguiculata* sequence (NCBI GI No. 4582783; SEQ ID NO:13). The data in Table 5 represents a calculation of the percent identity of the amino acid sequences set forth in SEQ ID NOs:2, 6 and 12 and the *Vigna unguiculata* sequence (NCBI GI No. 4582783; SEQ ID NO:13).

TABLE 5

Percent Identity of Amino Acid Sequences Deduced From the Nucleotide Sequences of cDNA Clones Encoding Polypeptides Homologous to Starch Synthase Isoform V

| SEQ ID NO. | Percent Identity to NCBI GI No. 4582783; SEQ ID NO:13 |
|---|---|
| 2 | 54.2 |
| 6 | 56.2 |
| 12 | 54.9 |

An N-terminal motif, [K(T/V/A)GGL], present in starch synthases and believed to be required for binding of ADP/ADP-glucose (Edwards et al., (1999) *Eur J Biochem* 266:724–736), is conserved among the sequences of FIG. 1 at consensus amino acid positions 493–497. A second very similar motif, [X(T/V)GGL], is found in starch synthase proteins close to the C-terminus (Edwards et al., (1999) *Eur J Biochem* 266:724–736). This second motif is conserved among the sequences of FIG. 1 at consensus amino acid positions 885–889.

Sequence alignments and percent identity calculations were performed using the Megalign program of the LASER-GENE bioinformatics computing suite (DNASTAR Inc., Madison, Wis.). Multiple alignment of the sequences was performed using the ClustalV method of alignment (Higgins and Sharp (1989) *CABIOS*. 5:151–153) with the following parameters: GAP PENALTY=9, GAP LENGTH PENALTY=9. These gap penalty values were used instead of the default parameter values of 10, in order to better align the shorter *Vigna unguiculata* sequence (NCBI GI No. 4582783; SEQ ID NO:13) with the longer corn, rice and wheat sequences. For pairwise alignments using the ClustaIV method the following default parameters were used: KTUPLE 1, GAP PENALTY=3, WINDOW=5 and DIAGONALS SAVED=5. Sequence alignments and BLAST scores and probabilities indicate that the nucleic acid sequences of SEQ ID NOs:1, 5 and 11 encode starch synthase isoform V proteins from corn, rice and wheat, respectively.

A maize sequence for a partial starch synthase isoform V protein, containing 735 amino acids, has been disclosed previously (Kossmann et al., PCT WO 97/26362 and U.S. Pat. No. 6,211,436). Except for differences with the first two amino acid residues of the sequence of Kossmann et al., the remaining sequence from amino acid #3 to #735 is identical to the corresponding amino acid sequence of SEQ ID NO:2, from amino acid #177 to #909.

Example 4

Expression of Recombinant DNA Constructs in Monocot Cells

A recombinant DNA construct comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of plant cDNA or cDNA libraries using appropriate oligonucleotide primers. Cloning sites (Ncol or Smal) can be incorporated into the oligonucleotides to provide proper orientation of the DNA fragment when inserted into the digested vector pML103 as described below. Amplification is then performed in a standard PCR. The amplified DNA is then digested with restriction enzymes Ncol and Smal and fractionated on an agarose gel. The appropriate band can be isolated from the gel and combined with a 4.9 kb Ncol-Smal fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb Smal-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptide, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional 2 weeks the tissue can be transferred to fresh N6 medium containing bialaphos. After 6 weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of plant cDNA or cDNA libraries using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl₂ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Recombinant DNA Constructs in Microbial Cells

The cDNA fragment of this gene may be generated by polymerase chain reaction (PCR) of plant cDNA or cDNA libraries using appropriate oligonucleotide primers. The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Starch synthase activity can be measured in vitro using E. coli extracts and the method of Edwards et al., (1999) Eur J Biochem 266:724–736. Alternatively, the mutant E. coli strain, HfrG6MD2, in which all the glycogen synthesis genes have been deleted, can be used to assay for starch synthase activity in vivo by iodine staining, as described in Kossmann et al., PCT WO 97/26362 and U.S. Pat. No. 6,211,436.

Example 7

Expression of Recombinant DNA Constructs in Yeast Cells

The polypeptides encoded by the polynucleotides of the instant invention may be expressed in a yeast (Saccharomyces cerevisiae) strain YPH. Plant cDNA or cDNA libraries may be used as template to amplify the portion encoding the starch synthase isoform V protein. Amplification may be performed using the GC melt kit (Clontech) with a 1 M final concentration of GC melt reagent and using a Perkin Elmer 9700 thermocycler. The amplified insert may then be incubated with a modified pRS315 plasmid (NCBI General Identifier No. 984798; Sikorski, R. S. and Hieter, P. (1989) Genetics 122:19–27) that has been digested with Not I and Spe I. Plasmid pRS315 has been previously modified by the insertion of a bidirectional gal1/10 promoter between the Xho I and Hind III sites. The plasmid may then be transformed into the YPH yeast strain using standard procedures where the insert recombines through gap repair to form the desired transformed yeast strain (Hua, S. B. et al. (1997) Plasmid 38:91–96).

Yeast cells may be prepared according to a modification of the methods of Pompon et al. (Pompon, D. et al. (1996) Meth. Enz. 272:51–64). Briefly, a yeast colony will be grown overnight (to saturation) in SG (-Leucine) medium at 30° C. with good aeration. A 1:50 dilution of this culture will be made into 500 mL of YPGE medium with adenine supplementation and allowed to grow at 30° C. with good aeration to an $OD_{600}$ of 1.6 (24–30 h). Fifty mL of 20% galactose will be added, and the culture allowed to grow overnight at 30° C. The cells will be recovered by centrifugation at 5,500 rpm for five minutes in a Sorvall GS-3 rotor. The cell pellet resuspended in 500 mL of 0.1 M potassium phosphate buffer (pH 7.0) and then allowed to grow at 30° C. for another 24 hours.

The cells may be recovered by centrifugation as described above and the presence of the polypeptide of the instant invention determined by HPLC/mass spectrometry or any other suitable method.

Example 8

Expression of Recombinant DNA Constructs in Insect Cells

The cDNA fragment of this gene may be generated by polymerase chain reaction (PCR) of plant cDNA or cDNA libraries using appropriate oligonucleotide primers. The cDNAs encoding the instant polypeptides may be introduced into the baculovirus genome itself. For this purpose the cDNAs may be placed under the control of the polyhedron promoter, the IE1 promoter, or any other one of the baculovirus promoters. The cDNA, together with appropriate leader sequences is then inserted into a baculovirus transfer vector using standard molecular cloning techniques. Following transformation of *E. coli* DH5α, isolated colonies are chosen and plasmid DNA is prepared and is analyzed by restriction enzyme analysis. Colonies containing the appropriate fragment are isolated, propagated, and plasmid DNA is prepared for cotransfection.

*Spodoptera frugiperda* cells (Sf-9) are propagated in ExCell® 401 media (JRH Biosciences, Lenexa, Kans.) supplemented with 3.0% fetal bovine serum. Lipofectin® (50 μL at 0.1 mg/mL, Gibco/BRL) is added to a 50 μL aliquot of the transfer vector containing the toxin gene (500 ng) and linearized polyhedrin-negative AcNPV (2.5 μg, Baculogold® viral DNA, Pharmigen, San Diego, Calif.). Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), *Baculovirus Expression Vectors: A Laboratory Manual*, W. H. Freeman and Company, New York.). Sf-9 cells in 35 mM petri dishes (50% monolayer) are inoculated with 100 μL of a serial dilution of the viral suspension, and supernatant fluids are collected at 5 days post infection. In order to prepare larger quantities of virus for characterization, these supernatant fluids are used to inoculate larger tissue cultures for large-scale propagation of recombinant viruses.

What is claimed is:

1. An isolated polynucleotide comprising:
   (a) a nucleotide sequence encoding a polypeptide having starch synthase activity, wherein the amino acid sequence of the polypeptide and the amino acid sequence of SEQ ID NO:12 have at least 85% sequence identity, based on the ClustalV alignment method with pairwise alignment default parameters of KTUPLE=1, GAP PENALTY=3, WINDOW=5 and DIAGONALS SAVED=5, or
   (b) the complement of the nucleotide sequence of (a), wherein the complement and the nucleotide sequence consist of the same number of nucleotides and are 100% complementary.

2. The polynucleotide of claim 1, wherein the amino acid sequence of the polypeptide and the amino acid sequence of SEQ ID NO:12 have at least 90% sequence identity, based on the ClustalV alignment method with the pairwise alignment default parameters.

3. The polynucleotide of claim 1, wherein the amino acid sequence of the first polypeptide and the amino acid sequence of SEQ ID NO:12 have at least 95% identity, based on the ClustalV alignment method with the pairwise alignment default parameters.

4. The polynucleotide of claim 1, wherein the amino acid sequence of the polypeptide comprises the amino acid sequence SEQ ID NO:12.

5. The polynucleotide of claim 1 wherein the nucleotide sequence comprises the nucleotide sequence of SEQ ID NO:11.

6. A vector comprising the polynucleotide of claim 1.

7. A recombinant DNA construct comprising the polynucleotide of claim 1 operably linked to at least one regulatory sequence.

8. A method for transforming a cell, comprising transforming a cell with the polynucleotide of claim 1.

9. A cell comprising the recombinant DNA construct of claim 7.

10. A method for producing a plant comprising transforming a plant cell with the polynucleotide of claim 1 and regenerating a plant from the transformed plant cell.

11. A plant comprising the recombinant DNA construct of claim 7.

12. A seed comprising the recombinant DNA construct of claim 7.

* * * * *

UNITED STATES PATENT AND TRADEMARK OFFICE
CERTIFICATE OF CORRECTION

PATENT NO. : 6,849,781 B2  Page 1 of 1
APPLICATION NO. : 10/163214
DATED : February 1, 2005
INVENTOR(S) : Stephen M. Allen, Karlene H. Butler and Catherine J. Thorpe It is certified that error appears in the above-identified patent and that said Letters Patent is hereby corrected as shown below:

Column 63, Claim 3, line 58: delete "first".

Signed and Sealed this

Thirtieth Day of January, 2007

JON W. DUDAS
*Director of the United States Patent and Trademark Office*

SEQUENCE LISTING

<160> NUMBER OF SEQ ID NOS: 13

<210> SEQ ID NO 1
<211> LENGTH: 3430
<212> TYPE: DNA
<213> ORGANISM: Zea mays

<400> SEQUENCE: 1

```
gcacgagccg cctctggctc tccttcctcc gccttccgcg cgcagcgcag agcgcacggg      60 acaccgccg cccacgcctt ccgccccaga cccactgcac gtgcacggac acgcgaccta     120
gcccacacat ccactccgct ttttccaacc gccgccacg cgaaccccga cgcggtcgcc     180
tcgagctcca ctccgtttac cctgcaaccc catcctcctc ggcttcccat gtcgtgctcg     240
gcggcggcgg gcgccgaggc caccgctctc ctgttccgca gcgccgctcc gtccacgatc     300
gtcgggcgtc accgcctcgc tatgtctcgc cggacttcgc gccgaaacct caggactggt     360
gtgcaccctc atcagaagag tgcacctagt gctaaccatc gtaacagggc tagcattcag     420
agagatagag catcagcttc cattgatgaa gaacagaaac agatgtctga agatgaaaat     480
ggcctactag acattcaact ggaagatctg gtaggaatga tacagaatac ccagaagaat     540
atattgcttc tgaatcaagc tcgtcttcaa gcattggaac gtgctgacaa aattcttaaa     600
gagaaagaaa ctttgcaaca gaagataaac attttagaga tgaaactgtc agaaacaggt     660
aaacaatctg tgctttctag tgaagtaaag tctgatgaag agagtctgga gtttgatgtc     720
gtaaaggaag agaatatgct actgaaggat gagatgaatt ttctaaaagg aaagcttatt     780
gagataactg agacagagga gagtctattc aagttggaga aagagtgtgc tcttctaaat     840
gcttccctta gggagctcga gtgtacatcc acttctgccc aatctgatgt gttgaaactt     900
ggccctctgc aacaagatgc ctggtgggag aaagtagaaa atttggaaga cttgcttgat     960
tccacagcaa accaagtgga gcatgcttct ttgacgctag atggttaccg tgatttccag    1020
gataaggttg acaaactaaa agcatcattg ggaacaacaa acgtatcaga gttctgtctt    1080
tatttggttg atattttgca gcaaagggta aaatcagtag aagagcgctt tcaagcatgt    1140
aatcatgaaa tgcattcaca aattgaactt tatgaacact caatagtgga gtttcatggt    1200
actctcagca aactaataaa tgaaagtgag aaaaagtcaa tggagcatta tgcagaaggc    1260
atgccatcag agttctggag taggatctct cttctgattg atgggtggtc gcttgagaag    1320
```

```
aaaatatcca ttaatgatgc aagtatgttg agagaaatgg cttggaaaag ggataatcgc    1380
ctccgggaag cttacttgtc atccagagga atggaagaga gggaactgat agatagtttt    1440
ctaaagatgg cactaccagg aacaagttct ggtttgcaca ttgtccacat agcagcagag    1500
atggctcctg tcgcaaaggt tggtggtctg gcagatgtga tctctggtct tgggaaggca    1560
cttcaaaaaa aggggcacct tgtagagatt attcttccca aatatgattg catgcagcat    1620
aaccaaataa ataatcttaa ggttctagat gttgtggtga agtcttactt tgaaggaaat    1680
atgtttgcca acaagatatg gactggaact gttgaaggtc ttccggtcta ctttattgaa    1740
ccgcaacatc caggtaagtt cttctggagg gcacaatact acggagagca tgatgacttc    1800
aaacgttttt cgtactttag ccgtgttgca ctggaattgc tttaccaatc tgggaagaaa    1860
gttgacataa ttcactgcca tgactggcag actgcatttg ttgcacctct ttactgggat    1920
gtatatgcaa acctgggctt caactcagct agaatttgtt ttacctgtca caattttgaa    1980
tatcaaggaa tcgctccagc tcaggactta gcatattgtg gtcttgatgt tgatcacctg    2040
gatagaccag acagaatgcg ggataattca catggcagaa taatgttgt taagggtgca    2100 gttgtatatt ccaacattgt gacaactgta tcaccaacat atgcacaaga ggttcgctca    2160
gagggtgggc gtgggctcca agatacactc aaagtgcact ccaagaaatt tgttggaata    2220
cttaatggca ttgacacaga tacttggaat ccgtctacgg ataggtttct caaggttcaa    2280
tacagtgcta atgatctata tggaaagtca gcaaacaaag cagctcttag gaagcagttg    2340
aagcttgctt ccacacaagc ttctcaacca ttagttggtt gcattacgag gctagttcct    2400
caaaagggtg tacatctcat caggcatgca atatataaaa taactgagtt gggtggtcaa    2460
tttgttctgc tgggttcaag tccagtacag catatccaga gagagttcga gggtattgcg    2520
gaccaatttc agaacaacaa caatgtcagg ctgcttttga agtatgatga tgctctggca    2580
catatgatct ttgcagcatc agacatgttc attgttcctt ctatgtttga accatgtggc    2640
ctcactcaga tggtagctat gcgatatggt tctgtgccag ttgttcggag aaccggcggt    2700
ttgaatgaca gtgtcttcga tttgacgat gaaacgatac ccatggaggt gcgaaatggc    2760 ttcaccttttt tgaaggctga tgagcaggat tttggtaatg cactggaaag agctttcaac    2820
tactaccaca gaaaacctga gtttggaaaa cagttggtgc agaaagacat gaagatagat    2880
ttcagctggg atacttcagt ttctcaatac gaagaaatct atcagaaaac agccactcga    2940
gccagggcag cggcataaac agcagagaca ttgagacagt tccctgctgt ctccatgaag    3000
tctcctagat gctgtgctta accgtatggt aaagaaatat ggtctgtatc agctcagaat    3060
taagcatctg ccgaggaagc gcggtgcatc cggactcggg tgtacaaggg gcgacgtggc    3120
gttacgtgca gtccccaacg aagcaaagag acagaagtac agctgtacag aacggatatc    3180
ttgtgaagca cacattggga tcaggacgtt tggtgctgca gctactttcg gtgcagaagc    3240
acatatatac gagacctgcc agggcgagca aatacccagt tatacacgcg attgctcagc    3300
tctatcaagc tgtgaattga agatttctta tagtgtattc acgcgacgtt ttcataaact    3360
agtgtgagtt atgtactctg accagtgacc agtgcgaagt ctgtgttgtc tcaaaaaaaa    3420
aaaaaaaag                                                          3430

<210> SEQ ID NO 2
<211> LENGTH: 909
<212> TYPE: PRT
<213> ORGANISM: Zea mays
```

```
<400> SEQUENCE: 2

Met Ser Cys Ser Ala Ala Gly Ala Glu Ala Thr Ala Leu Leu Phe
 1               5                  10                  15

Arg Ser Ala Ala Pro Ser Thr Ile Val Gly Arg His Arg Leu Ala Met
            20                  25                  30

Ser Arg Arg Thr Ser Arg Arg Asn Leu Arg Thr Gly Val His Pro His
        35                  40                  45

Gln Lys Ser Ala Pro Ser Ala Asn His Arg Asn Arg Ala Ser Ile Gln
    50                  55                  60

Arg Asp Arg Ala Ser Ala Ser Ile Asp Glu Glu Gln Lys Gln Met Ser
65                  70                  75                  80

Glu Asp Glu Asn Gly Leu Leu Asp Ile Gln Leu Glu Asp Leu Val Gly
                85                  90                  95

Met Ile Gln Asn Thr Gln Lys Asn Ile Leu Leu Asn Gln Ala Arg
                100                 105                 110

Leu Gln Ala Leu Glu Arg Ala Asp Lys Ile Leu Lys Glu Lys Glu Thr
            115                 120                 125

Leu Gln Gln Lys Ile Asn Ile Leu Glu Met Lys Leu Ser Glu Thr Gly
        130                 135                 140

Lys Gln Ser Val Leu Ser Ser Glu Val Lys Ser Asp Glu Glu Ser Leu
145                 150                 155                 160

Glu Phe Asp Val Val Lys Glu Glu Asn Met Leu Leu Lys Asp Glu Met
                165                 170                 175

Asn Phe Leu Lys Gly Lys Leu Ile Glu Ile Thr Glu Thr Glu Glu Ser
                180                 185                 190

Leu Phe Lys Leu Glu Lys Glu Cys Ala Leu Leu Asn Ala Ser Leu Arg
        195                 200                 205

Glu Leu Glu Cys Thr Ser Thr Ser Ala Gln Ser Asp Val Leu Lys Leu
            210                 215                 220

Gly Pro Leu Gln Gln Asp Ala Trp Trp Glu Lys Val Glu Asn Leu Glu
225                 230                 235                 240

Asp Leu Leu Asp Ser Thr Ala Asn Gln Val Glu His Ala Ser Leu Thr
                245                 250                 255

Leu Asp Gly Tyr Arg Asp Phe Gln Asp Lys Val Asp Lys Leu Lys Ala
                260                 265                 270

Ser Leu Gly Thr Thr Asn Val Ser Glu Phe Cys Leu Tyr Leu Val Asp
            275                 280                 285

Ile Leu Gln Gln Arg Val Lys Ser Val Glu Glu Arg Phe Gln Ala Cys
        290                 295                 300

Asn His Glu Met His Ser Gln Ile Glu Leu Tyr Glu His Ser Ile Val
305                 310                 315                 320

Glu Phe His Gly Thr Leu Ser Lys Leu Ile Asn Glu Ser Glu Lys Lys
                325                 330                 335

Ser Met Glu His Tyr Ala Glu Gly Met Pro Ser Glu Phe Trp Ser Arg
                340                 345                 350

Ile Ser Leu Leu Ile Asp Gly Trp Ser Leu Glu Lys Lys Ile Ser Ile
        355                 360                 365

Asn Asp Ala Ser Met Leu Arg Glu Met Ala Trp Lys Arg Asp Asn Arg
370                 375                 380

Leu Arg Glu Ala Tyr Leu Ser Ser Arg Gly Met Glu Glu Arg Glu Leu
385                 390                 395                 400

Ile Asp Ser Phe Leu Lys Met Ala Leu Pro Gly Thr Ser Ser Gly Leu
                405                 410                 415
```

```
His Ile Val His Ile Ala Ala Glu Met Ala Pro Val Ala Lys Val Gly
            420                 425                 430

Gly Leu Ala Asp Val Ile Ser Gly Leu Gly Lys Ala Leu Gln Lys Lys
            435                 440                 445

Gly His Leu Val Glu Ile Ile Leu Pro Lys Tyr Asp Cys Met Gln His
            450                 455                 460

Asn Gln Ile Asn Asn Leu Lys Val Leu Asp Val Val Lys Ser Tyr
465                 470                 475                 480

Phe Glu Gly Asn Met Phe Ala Asn Lys Ile Trp Thr Gly Thr Val Glu
                485                 490                 495

Gly Leu Pro Val Tyr Phe Ile Glu Pro Gln His Pro Gly Lys Phe Phe
                500                 505                 510

Trp Arg Ala Gln Tyr Tyr Gly Glu His Asp Asp Phe Lys Arg Phe Ser
                515                 520                 525

Tyr Phe Ser Arg Val Ala Leu Glu Leu Leu Tyr Gln Ser Gly Lys Lys
    530                 535                 540

Val Asp Ile Ile His Cys His Asp Trp Gln Thr Ala Phe Val Ala Pro
545                 550                 555                 560

Leu Tyr Trp Asp Val Tyr Ala Asn Leu Gly Phe Asn Ser Ala Arg Ile
                565                 570                 575

Cys Phe Thr Cys His Asn Phe Glu Tyr Gln Gly Ile Ala Pro Ala Gln
                580                 585                 590

Asp Leu Ala Tyr Cys Gly Leu Asp Val Asp His Leu Asp Arg Pro Asp
    595                 600                 605

Arg Met Arg Asp Asn Ser His Gly Arg Ile Asn Val Val Lys Gly Ala
    610                 615                 620

Val Val Tyr Ser Asn Ile Val Thr Thr Val Ser Pro Thr Tyr Ala Gln
625                 630                 635                 640

Glu Val Arg Ser Glu Gly Gly Arg Gly Leu Gln Asp Thr Leu Lys Val
                645                 650                 655

His Ser Lys Lys Phe Val Gly Ile Leu Asn Gly Ile Asp Thr Asp Thr
                660                 665                 670

Trp Asn Pro Ser Thr Asp Arg Phe Leu Lys Val Gln Tyr Ser Ala Asn
    675                 680                 685

Asp Leu Tyr Gly Lys Ser Ala Asn Lys Ala Ala Leu Arg Lys Gln Leu
    690                 695                 700

Lys Leu Ala Ser Thr Gln Ala Ser Gln Pro Leu Val Gly Cys Ile Thr
705                 710                 715                 720

Arg Leu Val Pro Gln Lys Gly Val His Leu Ile Arg His Ala Ile Tyr
                725                 730                 735

Lys Ile Thr Glu Leu Gly Gly Gln Phe Val Leu Leu Gly Ser Ser Pro
                740                 745                 750

Val Gln His Ile Gln Arg Glu Phe Glu Gly Ile Ala Asp Gln Phe Gln
                755                 760                 765

Asn Asn Asn Asn Val Arg Leu Leu Leu Lys Tyr Asp Asp Ala Leu Ala
770                 775                 780

His Met Ile Phe Ala Ala Ser Asp Met Phe Ile Val Pro Ser Met Phe
785                 790                 795                 800

Glu Pro Cys Gly Leu Thr Gln Met Val Ala Met Arg Tyr Gly Ser Val
                805                 810                 815

Pro Val Val Arg Arg Thr Gly Gly Leu Asn Asp Ser Val Phe Asp Leu
                820                 825                 830
```

```
Asp Asp Glu Thr Ile Pro Met Glu Val Arg Asn Gly Phe Thr Phe Leu
        835                 840                 845

Lys Ala Asp Glu Gln Asp Phe Gly Asn Ala Leu Glu Arg Ala Phe Asn
    850                 855                 860

Tyr Tyr His Arg Lys Pro Glu Val Trp Lys Gln Leu Val Gln Lys Asp
865                 870                 875                 880

Met Lys Ile Asp Phe Ser Trp Asp Thr Ser Val Ser Gln Tyr Glu Glu
            885                 890                 895

Ile Tyr Gln Lys Thr Ala Thr Arg Ala Arg Ala Ala Ala
            900                 905

<210> SEQ ID NO 3
<211> LENGTH: 375
<212> TYPE: DNA
<213> ORGANISM: Oryza sativa
<220> FEATURE:
<221> NAME/KEY: unsure
<222> LOCATION: (245)
<223> OTHER INFORMATION: n = A, C, G or T
<220> FEATURE:
<221> NAME/KEY: unsure
<222> LOCATION: (299)
<223> OTHER INFORMATION: n = A, C, G or T
<220> FEATURE:
<221> NAME/KEY: unsure
<222> LOCATION: (314)..(315)
<223> OTHER INFORMATION: n = A, C, G or T
<220> FEATURE:
<221> NAME/KEY: unsure
<222> LOCATION: (349)
<223> OTHER INFORMATION: n = A, C, G or T
<220> FEATURE:
<221> NAME/KEY: unsure
<222> LOCATION: (354)
<223> OTHER INFORMATION: n = A, C, G or T
<220> FEATURE:
<221> NAME/KEY: unsure
<222> LOCATION: (363)
<223> OTHER INFORMATION: n = A, C, G or T
<220> FEATURE:
<221> NAME/KEY: unsure
<222> LOCATION: (366)
<223> OTHER INFORMATION: n = A, C, G or T
<220> FEATURE:
<221> NAME/KEY: unsure
<222> LOCATION: (370)
<223> OTHER INFORMATION: n = A, C, G or T

<400> SEQUENCE: 3
gtcaggaaaa gggatagttg tcttcgggaa gcatacttgt catgcagagg tatgaaagat      60
agggaaattg tggacaattt tctaaagatc acattgccag ggactagttc tggcttgcac     120
atcatccaca tagcagcaga gatggctcct gttgcaaagg ttggtggttt ggcggatgtg     180
atatctggtc ttggcaaggc acttcagaaa aagggccacc tagtagagat tattcttcca     240
aaatntgact gcatgcagaa tgaccaagtt aataacctta aggttttaga tgttgtggna     300
caatcctact ttgnnggaaa tttgttcaac aacaaaatat ggactgggnc tgtngaaggc     360
ctnccngtcn attta                                                      375

<210> SEQ ID NO 4
<211> LENGTH: 121
<212> TYPE: PRT
<213> ORGANISM: Oryza sativa
<220> FEATURE:
<221> NAME/KEY: UNSURE
<222> LOCATION: (80)
<223> OTHER INFORMATION: Xaa = ANY AMINO ACID
<220> FEATURE:
```

```
<221> NAME/KEY: UNSURE
<222> LOCATION: (98)
<223> OTHER INFORMATION: Xaa = ANY AMINO ACID
<220> FEATURE:
<221> NAME/KEY: UNSURE
<222> LOCATION: (103)
<223> OTHER INFORMATION: Xaa = ANY AMINO ACID
<220> FEATURE:
<221> NAME/KEY: UNSURE
<222> LOCATION: (115)
<223> OTHER INFORMATION: Xaa = ANY AMINO ACID

<400> SEQUENCE: 4

Lys Arg Asp Ser Cys Leu Arg Glu Ala Tyr Leu Ser Cys Arg Gly Met
  1               5                  10                  15

Lys Asp Arg Glu Ile Val Asp Asn Phe Leu Lys Ile Thr Leu Pro Gly
             20                  25                  30

Thr Ser Gly Leu His Ile Ile His Ile Ala Ala Glu Met Ala Pro
         35                  40                  45

Val Ala Lys Val Gly Gly Leu Ala Asp Val Ile Ser Gly Leu Gly Lys
     50                  55                  60

Ala Leu Gln Lys Lys Gly His Leu Val Glu Ile Ile Leu Pro Lys Xaa
 65                  70                  75                  80

Asp Cys Met Gln Asn Asp Gln Val Asn Asn Leu Lys Val Leu Asp Val
                 85                  90                  95

Val Xaa Gln Ser Tyr Phe Xaa Gly Asn Leu Phe Asn Asn Lys Ile Trp
             100                 105                 110

Thr Gly Xaa Val Glu Gly Leu Pro Val
         115                 120

<210> SEQ ID NO 5
<211> LENGTH: 3453
<212> TYPE: DNA
<213> ORGANISM: Oryza sativa

<400> SEQUENCE: 5
gcttacaccg gacgccgcgc ccccccttcc ccagcctccg catccgattc ccatggcgtg     60
cttggcggcg ggcgccgagg cggcccctct cctcttccgg cggcggctag cgccgtcccc    120
agtcgccgcg cgccgccgcc ttctcgtgtc gtgccgagct cgccgccgcg gtctcaggac    180
tgctgcagaa cttcctcgga agagtacaag taatgataaa caccataata gggtgaatat    240
gcagagagat gaagcatctg tttccagtga taaagaacgg caagagaaat atggagatga    300
aaatggtata tcaaaccttc aattggaaga tttgatacaa atgatacaaa acactgagaa    360
gaatataatg cttctgaatc aagctcgtct tcaagcattg gaacatgttg aaacagttct    420
taaagaaaaa gaagacttac agaggaagtt gaaaattttg gagacgagat tgtcagaaac    480
agatgcacgg cttaagcttt cagctgaagg gcagttcggt actgagatta atgactctct    540
accagtactg gaattagatg atataaagga agagaatatg ctactgaagg atgacataca    600
atttctgaaa acaatgctta ttgaggttgc tgagacagag aacagtatat tcacattaga    660
gaaggagcgt gctcttttag atgcttcgct tagggagctg gagtctagat ttatagatgc    720
ccaagcagat atgttgaagt ctgatcctag gcagtatgat gcatggtggg agaaagtaga    780
aaatttgggg gacttgcttg agactgcaac aaacaaagta gagaatgctg ctatggttct    840
gggacgcaat catgatttgg aagataaggt cgacaaacta gaggcatcgt ggctgaagc     900
aaatatatca aagttctctt gttatttttgt tgatcttttg caggaaaaga taaaatcagt    960
agaagagcgc ttccaagtat gtaatcatga aatgcattct caaattgaac tctatgagaa   1020
```

-continued

```
ttcaatagcg gaatttcacg atattcttag caagctagtg gaggaaactg agaaacgatc      1080
actagagcat tcagcaagta gcatgccttc agaattgtgg agtaggatat ctcttctgat      1140
tgatggttgg ttgctcgaga agagaatatc ctacaatgat gcaaatacat tacgggaaat      1200
ggtcaggaaa agggatagtt gtcttcggga agcatacttg tcatgcagag gtatgaaaga      1260
tagggaaatt gtggacaatt ttctaaagat cacattgcca gggactagtt ctggcttgca      1320
catcatccac atagcagcag agatggctcc tgttgcaaag gttggtggtt tggcggatgt      1380
gatatctggt cttggcaagg cacttcagaa aaagggccac ctagtagaga ttattcttcc      1440
aaaatatgac tgcatgcaga atgaccaagt taataacctt aaggttttag atgttgttgt      1500
acaatcctac tttgaaggaa atttgttcaa caacaaaata tggactggga ctgttgaagg      1560
ccttccagtc tattttatcg agccacaaca tccagcaaaa ttcttttgga gggcacaata      1620
ctatggagaa cacgatgact ttaaacgttt gcatacttc agccgtgcag cactggaatt      1680
actttaccaa tcgcagaaga aaattgacat catccattgc catgactggc agactgcatt      1740
tgtggcacct ctttattggg aagcatatgc aaatctgggc ttcaactcag ctagaatttg      1800
cttcacctgc cataattttg aatatcaagg agctgctcct gctcaagatt tagcatgctg      1860
tggccttgat gttcagcaac ttgatagga agacaggatg cgggacaatt cacatggcag      1920
aataaatgtt gtcaagggtg caattgtgta ttccaacatt gtgacaactg tatcaccaac      1980
atatgcacta gaggtgcgat cagagggtgg acgtggacta caagattcac tcaaattaca      2040
ttccaggaaa tttgttggga tacttaatgg aatcgacaca gacacatgga atccttcaac      2100
agatagacat ctcaaggttc aatataatgc taatgatctc cagggtaagg cagcaaacaa      2160
agcagctctc agaaagcagc taaacttatc ttctacaaat gcttctcaac cactggttgg      2220
gtgtattaca aggctagttc ctcaaaaggg tgtacatctc atcaggcatg caatatacaa      2280
aacagctgag ctaggaggac agtttgttct tctgggctca agtccagtac cacacattca      2340
aagagagttt gagggtattg cagaccattt tcagaacaat aacaatatcc gactgctttt      2400
gaagtatgat gattctttat cccattggat ttatgcagca tctgacatgt tcattgttcc      2460
atccatgttt gagccatgtg gcctcacaca gatgattgcc atgagatatg gttctgtgcc      2520
gattgttcgg aaaaccggtg gattgaatga cagtgtcttc gatttcgacg acgaaacgat      2580
acctaaggag ctgcggaatg gctttacgtt tgtgcatcct gatgaaaagg ctctaagtgg      2640
tgcaatggag agagcgttca actactacaa tagaaagcct gaggtctgga acagctggt      2700 gcagaaggac atgaggatag atttcagctg ggcctcttca gcttcccagt acgaagatat      2760
ctatcaaaga gcagtggctc gagcgagggc agcagcatga actctggcgg tttagtgaga      2820
cctgagcctt tctctgacgc ggcgcttgat gccacaggca cagattctgc cttctgaaga      2880
agccgcacca tgcacctctc tgatgtgcga acatggcttc atctgcagct tcgattcttg      2940
gaatggaacc caagatattt aaagacatga tccgtcagac tcatgcagga agccgagatg      3000
ttccatagtg cagttatgga atggtcgaag aactaaaatc ttggcaccca ttgtcgtgtc      3060
ccagtgacag tgtggactat acagttatat aacttatagt acgtgattgc tcagtcgtga      3120
aatttcacta gcctcgatat atttatcatg cgctacggtg aaatgataag ttttgttctt      3180
tgtatcactt gcagtgtgct tgttatttg tgcaaagtcg tgtgtgttgt ctatagaata      3240
ttctttcgtc aaaagcaaag agatgagaga cagaccctgt tttttttcct gtttgaactc      3300
tgaaatgtag aaaaaaattt cataggctct ttgaaatttt tttagagaac actacaattc      3360
```

```
atgtagaaaa tttcatgttt ttcttctctg atgtactccc accgttaagg aaagggata    3420 tttccattcg gtcaaaaaaa aaaaaaaaaa aaa                                 3453
```

<210> SEQ ID NO 6
<211> LENGTH: 915
<212> TYPE: PRT
<213> ORGANISM: Oryza sativa

<400> SEQUENCE: 6

```
Met Ala Cys Leu Ala Ala Gly Ala Glu Ala Ala Pro Leu Leu Phe Arg
 1               5                  10                  15

Arg Arg Leu Ala Pro Ser Pro Val Ala Ala Arg Arg Leu Leu Val
             20                  25                  30

Ser Cys Arg Ala Arg Arg Gly Leu Arg Thr Ala Ala Glu Leu Pro
             35                  40                  45

Arg Lys Ser Thr Ser Asn Asp Lys His His Asn Arg Val Asn Met Gln
     50                  55                  60

Arg Asp Glu Ala Ser Val Ser Ser Asp Lys Glu Arg Gln Glu Lys Tyr
 65                  70                  75                  80

Gly Asp Glu Asn Gly Ile Ser Asn Leu Gln Leu Glu Asp Leu Ile Gln
                 85                  90                  95

Met Ile Gln Asn Thr Glu Lys Asn Ile Met Leu Leu Asn Gln Ala Arg
            100                 105                 110

Leu Gln Ala Leu Glu His Val Glu Thr Val Leu Lys Glu Lys Glu Asp
        115                 120                 125

Leu Gln Arg Lys Leu Lys Ile Leu Glu Thr Arg Leu Ser Glu Thr Asp
    130                 135                 140

Ala Arg Leu Lys Leu Ser Ala Glu Gly Gln Phe Gly Thr Glu Ile Asn
145                 150                 155                 160

Asp Ser Leu Pro Val Leu Glu Leu Asp Asp Ile Lys Glu Glu Asn Met
                165                 170                 175

Leu Leu Lys Asp Asp Ile Gln Phe Leu Lys Thr Met Leu Ile Glu Val
            180                 185                 190

Ala Glu Thr Glu Asn Ser Ile Phe Thr Leu Glu Lys Glu Arg Ala Leu
        195                 200                 205

Leu Asp Ala Ser Leu Arg Glu Leu Glu Ser Arg Phe Ile Asp Ala Gln
    210                 215                 220

Ala Asp Met Leu Lys Ser Asp Pro Arg Gln Tyr Asp Ala Trp Trp Glu
225                 230                 235                 240

Lys Val Glu Asn Leu Gly Asp Leu Leu Glu Thr Ala Thr Asn Lys Val
                245                 250                 255

Glu Asn Ala Ala Met Val Leu Gly Arg Asn His Asp Leu Glu Asp Lys
            260                 265                 270

Val Asp Lys Leu Glu Ala Ser Leu Ala Glu Ala Asn Ile Ser Lys Phe
        275                 280                 285

Ser Cys Tyr Phe Val Asp Leu Leu Gln Glu Lys Ile Lys Ser Val Glu
    290                 295                 300

Glu Arg Phe Gln Val Cys Asn His Glu Met His Ser Gln Ile Glu Leu
305                 310                 315                 320

Tyr Glu Asn Ser Ile Ala Glu Phe His Asp Ile Leu Ser Lys Leu Val
                325                 330                 335

Glu Glu Thr Glu Lys Arg Ser Leu Glu His Ser Ala Ser Ser Met Pro
            340                 345                 350

Ser Glu Leu Trp Ser Arg Ile Ser Leu Leu Ile Asp Gly Trp Leu Leu
```

-continued

```
                355                 360                 365
Glu Lys Arg Ile Ser Tyr Asn Asp Ala Asn Thr Leu Arg Glu Met Val
370                 375                 380
Arg Lys Arg Asp Ser Cys Leu Arg Glu Ala Tyr Leu Ser Cys Arg Gly
385                 390                 395                 400
Met Lys Asp Arg Glu Ile Val Asp Asn Phe Leu Lys Ile Thr Leu Pro
                405                 410                 415
Gly Thr Ser Ser Gly Leu His Ile Ile His Ile Ala Ala Glu Met Ala
            420                 425                 430
Pro Val Ala Lys Val Gly Gly Leu Ala Asp Val Ile Ser Gly Leu Gly
            435                 440                 445
Lys Ala Leu Gln Lys Lys Gly His Leu Val Glu Ile Ile Leu Pro Lys
450                 455                 460
Tyr Asp Cys Met Gln Asn Asp Gln Val Asn Asn Leu Lys Val Leu Asp
465                 470                 475                 480
Val Val Val Gln Ser Tyr Phe Glu Gly Asn Leu Phe Asn Asn Lys Ile
                485                 490                 495
Trp Thr Gly Thr Val Glu Gly Leu Pro Val Tyr Phe Ile Glu Pro Gln
            500                 505                 510
His Pro Ala Lys Phe Phe Trp Arg Ala Gln Tyr Tyr Gly Glu His Asp
            515                 520                 525
Asp Phe Lys Arg Phe Ala Tyr Phe Ser Arg Ala Ala Leu Glu Leu Leu
            530                 535                 540
Tyr Gln Ser Gln Lys Lys Ile Asp Ile Ile His Cys His Asp Trp Gln
545                 550                 555                 560
Thr Ala Phe Val Ala Pro Leu Tyr Trp Glu Ala Tyr Ala Asn Leu Gly
                565                 570                 575
Phe Asn Ser Ala Arg Ile Cys Phe Thr Cys His Asn Phe Glu Tyr Gln
                580                 585                 590
Gly Ala Ala Pro Ala Gln Asp Leu Ala Cys Cys Gly Leu Asp Val Gln
            595                 600                 605
Gln Leu Asp Arg Glu Asp Arg Met Arg Asp Asn Ser His Gly Arg Ile
610                 615                 620
Asn Val Val Lys Gly Ala Ile Val Tyr Ser Asn Ile Val Thr Thr Val
625                 630                 635                 640
Ser Pro Thr Tyr Ala Leu Glu Val Arg Ser Glu Gly Arg Gly Leu
                645                 650                 655
Gln Asp Ser Leu Lys Leu His Ser Arg Lys Phe Val Gly Ile Leu Asn
            660                 665                 670
Gly Ile Asp Thr Asp Thr Trp Asn Pro Ser Thr Asp Arg His Leu Lys
            675                 680                 685
Val Gln Tyr Asn Ala Asn Asp Leu Gln Gly Lys Ala Ala Asn Lys Ala
            690                 695                 700
Ala Leu Arg Lys Gln Leu Asn Leu Ser Ser Thr Asn Ala Ser Gln Pro
705                 710                 715                 720
Leu Val Gly Cys Ile Thr Arg Leu Val Pro Gln Lys Gly Val His Leu
                725                 730                 735
Ile Arg His Ala Ile Tyr Lys Thr Ala Glu Leu Gly Gly Gln Phe Val
                740                 745                 750
Leu Leu Gly Ser Ser Pro Val Pro His Ile Gln Arg Glu Phe Glu Gly
            755                 760                 765
Ile Ala Asp His Phe Gln Asn Asn Asn Ile Arg Leu Leu Leu Lys
770                 775                 780
```

Tyr Asp Asp Ser Leu Ser His Trp Ile Tyr Ala Ala Ser Asp Met Phe
785                 790                 795                 800

Ile Val Pro Ser Met Phe Glu Pro Cys Gly Leu Thr Gln Met Ile Ala
            805                 810                 815

Met Arg Tyr Gly Ser Val Pro Ile Val Arg Lys Thr Gly Gly Leu Asn
            820                 825                 830

Asp Ser Val Phe Asp Phe Asp Asp Glu Thr Ile Pro Lys Glu Leu Arg
            835                 840                 845

Asn Gly Phe Thr Phe Val His Pro Asp Glu Lys Ala Leu Ser Gly Ala
            850                 855                 860

Met Glu Arg Ala Phe Asn Tyr Tyr Asn Arg Lys Pro Glu Val Trp Lys
865                 870                 875                 880

Gln Leu Val Gln Lys Asp Met Arg Ile Asp Phe Ser Trp Ala Ser Ser
            885                 890                 895

Ala Ser Gln Tyr Glu Asp Ile Tyr Gln Arg Ala Val Ala Arg Ala Arg
            900                 905                 910

Ala Ala Ala
        915

<210> SEQ ID NO 7
<211> LENGTH: 546
<212> TYPE: DNA
<213> ORGANISM: Glycine max
<220> FEATURE:
<221> NAME/KEY: unsure
<222> LOCATION: (19)
<223> OTHER INFORMATION: n = A, C, G or T
<220> FEATURE:
<221> NAME/KEY: unsure
<222> LOCATION: (50)
<223> OTHER INFORMATION: n = A, C, G or T

<400> SEQUENCE: 7 gtttacctttt ggtgaattnc cggttgacca gggattaaac ggggctttgn tacggagcat      60
ttaatctctt caacaccaat ccttgagagt tggaagcaac ttgttcagaa ggacatgaac     120
atagatttca gctgggaaac atcatcagca caatatgagg agctctactt aaagtcttgt     180
ggctagagca aaggcagcaa aacttgctta attgagcaaa agaagggttc cctgtgcaat     240
ggttcaattt tgtcagtttc tacatagaga caagagttca gagttaaagc tcaatcagca     300
ggatttcact gagcatacca gccattcaag aacatctcag attgggaatg aatttaataa     360
aaaatattaa atgcaacatg gctgctgaaa gtatgctgca agttccacgc ctcatcaccc     420
agttactcct ttttccattt gaacgggggtt ttgatcatgg aagcaatctt tctcatatac     480
tttgatgaat tctaggtgat atttcaactt tactacgcct tgcaacattg cctgcagccc     540
ggggga                                                                546

<210> SEQ ID NO 8
<211> LENGTH: 33
<212> TYPE: PRT
<213> ORGANISM: Glycine max

<400> SEQUENCE: 8

Glu Ser Trp Lys Gln Leu Val Gln Lys Asp Met Asn Ile Asp Phe Ser
1               5                   10                  15

Trp Glu Thr Ser Ser Ala Gln Tyr Glu Glu Leu Tyr Leu Lys Ser Cys
            20                  25                  30

Gly

<210> SEQ ID NO 9
<211> LENGTH: 1275
<212> TYPE: DNA
<213> ORGANISM: Triticum aestivum

<400> SEQUENCE: 9

```
gcagaataaa tgctgttaag ggagcagttg tgtattcaaa catcgtgaca actgtctcgc      60
caacatatgc actagaggtt cgctcagagg gtgggcgtgg actccaagat acacttaaag    120
tacattccag gaaatttctt gggatactta atggaatcga cacagataca tggaaccctt    180
gcacagatag gtatctcaag gtccagtata atgctaagga tctccaggga aaggcagcca    240
acaaagcagc cctcagagag caactaaacc tggcttctgc atatccttca caaccactgg    300
ttggttgcat taccaggctg gttgctcaga agggtgtaca tcttatcagg catgcaatat    360
acaaaacagc tgaattagga ggacagtttg tccttctggg ttcaagtcca gtaccagaaa    420
ttcagaggga gtttgaaggt attgcagacc attttcagaa caacaacaat atccggctga    480
ttttgaagta tgatgatgcg ctgtctcatt gcatatatgc tgcgtctgac atgttcattg    540
ttccctctat atttgagcca tgtggcctca ctcagatgat agccatgaga tatggttctg    600
tgccaatcgt tcggaaaact ggtgggctga atgacagtgt ctttgacttc gatgacgaaa    660
caatacccat ggaggtgcgg aacggcttta catttgtcaa ggccgacgag cagggcctaa    720
gcagcgcgat ggagagggcg ttcaactgct cacgaggaa gcccgaggtg tggaaacagc    780
ttgtgcagaa agacatgacg atcgatttca gctgggacac ctcggcttcg cagtacgagg    840
acatctacca gaaggcggtg gctcgagcga gggcagtggc gtgagcacac acacacacgg    900
tagttggttc cctgatgcct ctctcccctg ccctgccctc atgatacaaa cggcactgga    960
cgaaatcgag ggatcatgga aacagaatca tatagcaagc tccatgctct cggcgcgcat   1020
ttccggtaag ggtgtgacgg tgtatcgctg gttatatgcg ctgtttattg aaggcagaac   1080
gcgagctaaa aatggagtag ctaccgtgaa ccctcaagat cgtagtatgc gcgctgttgt   1140
tggcataata ttggtgtaaa ttgtagtagg ctgtatattt tcttgagggg ttgcaacgga   1200
gctgtatgcg tgcagtgcag gctgcagagt cgcacgtatg tactgtatta tgcagaaaaa   1260
aaaaaaaaaa aaaaa                                                    1275
```

<210> SEQ ID NO 10
<211> LENGTH: 293
<212> TYPE: PRT
<213> ORGANISM: Triticum aestivum

<400> SEQUENCE: 10

```
Arg Ile Asn Ala Val Lys Gly Ala Val Val Tyr Ser Asn Ile Val Thr
 1               5                  10                  15
Thr Val Ser Pro Thr Tyr Ala Leu Glu Val Arg Ser Glu Gly Arg
             20                  25                  30
Gly Leu Gln Asp Thr Leu Lys Val His Ser Arg Lys Phe Leu Gly Ile
         35                  40                  45
Leu Asn Gly Ile Asp Thr Asp Thr Trp Asn Pro Cys Thr Asp Arg Tyr
     50                  55                  60
Leu Lys Val Gln Tyr Asn Ala Lys Asp Leu Gln Gly Lys Ala Ala Asn
 65                  70                  75                  80
Lys Ala Ala Leu Arg Glu Gln Leu Asn Leu Ala Ser Ala Tyr Pro Ser
                 85                  90                  95
```

```
Gln Pro Leu Val Gly Cys Ile Thr Arg Leu Val Ala Gln Lys Gly Val
            100                 105                 110

His Leu Ile Arg His Ala Ile Tyr Lys Thr Ala Glu Leu Gly Gly Gln
        115                 120                 125

Phe Val Leu Leu Gly Ser Ser Pro Val Pro Glu Ile Gln Arg Glu Phe
    130                 135                 140

Glu Gly Ile Ala Asp His Phe Gln Asn Asn Asn Ile Arg Leu Ile
145                 150                 155                 160

Leu Lys Tyr Asp Asp Ala Leu Ser His Cys Ile Tyr Ala Ala Ser Asp
                165                 170                 175

Met Phe Ile Val Pro Ser Ile Phe Glu Pro Cys Gly Leu Thr Gln Met
            180                 185                 190

Ile Ala Met Arg Tyr Gly Ser Val Pro Ile Val Arg Lys Thr Gly Gly
        195                 200                 205

Leu Asn Asp Ser Val Phe Asp Phe Asp Glu Thr Ile Pro Met Glu
    210                 215                 220

Val Arg Asn Gly Phe Thr Phe Val Lys Ala Asp Glu Gln Gly Leu Ser
225                 230                 235                 240

Ser Ala Met Glu Arg Ala Phe Asn Cys Tyr Thr Arg Lys Pro Glu Val
                245                 250                 255

Trp Lys Gln Leu Val Gln Lys Asp Met Thr Ile Asp Phe Ser Trp Asp
            260                 265                 270

Thr Ser Ala Ser Gln Tyr Glu Asp Ile Tyr Gln Lys Ala Val Ala Arg
        275                 280                 285

Ala Arg Ala Val Ala
    290

<210> SEQ ID NO 11
<211> LENGTH: 3386
<212> TYPE: DNA
<213> ORGANISM: Triticum aestivum

<400> SEQUENCE: 11
gccgtttgcc cgacgaatgg caccgtgcca cgcccacggc cctcctccgc ctccgccccc      60
gcctcgcccg cgcgcggagc acgagacacg ccacgcgctg gccccggcc accgccaccg      120
ccaccagtcc accaccacca gtccaccacc accactcttc agccccactc cactccccgc      180
cgctttccgg cccgccgccc gcttcaagct ccctcgccc caccagtcgc cctgcctctc      240
cctattcccc atggcgtgct ccgcggcggc gggcgtcgag cgaccgccc tcctgtcccc      300
gcgctgcccc gccccttccc cgcccgacgg ccgctcccgc cgccgcctcg ccctcgcttc      360
ccgcacgcgc caccgcagcc tcagggcggc cgcgcagcgc cctcacaaga gcgcaaccgg      420
cgccgacccc ctttataaca cagggccaa tgtgcggagc gacgaggcgt cggtttccgc      480
tgaaaaagaa cggcaaagga aatacaacga tggagatggc atatcaaacc ttaagctgga      540
agatttggta ggaatgatac agaacaccga agaatata cttcttttga atcaagcccg      600
tcttcaggca atgaacacg ctgataaagt tcttaaagaa aaggaagcct tgcagagaaa      660
gataaacatt ttagagacga ggttgtcaga aacagatgaa caacataagc tttcaagtga      720
agggaatttc agtgactctc cactagcatt ggagcttggt attctaaagg aagagaacat      780
tctactgaag gaggacatag aattttcaa aacaaagctt atagaggttg ccagataga      840
ggagggtata ttcaaattgg agaaggagca tgctcttta gatgcttccc ttagggagct      900
ggagtctagg tttatagccg cccaagcaga tacgatgaaa cttggtccta gggatgcctg      960
```

```
gtgggagaaa gtagaaaaat tggaagactt gcttgagacc acagcaaacc aagtagagca   1020
tgctgctgtg atattggacc acaatcatga tctgcaggat aggcttgaca atttagaggc   1080
atcactgcaa gcagcaaata tttcaaagtt ctcttgttct cttgttgatc ttttgcagca   1140
aaaggtcaaa ttggtagaag accgcttcca agcatgtaac agcgaaatgc attctcagat   1200
tgaactgtac gagcattcaa tagtggaatt tcatgatact cttagcaaac taatagagga   1260
aagtgagaaa agatcactgg agaattttac aggaaacatg ccttcggaac tatggagcaa   1320 aatttcccctt ttaattgatg gatggttact ggagaagaaa atatcttaca atgacgcaag   1380
tatgttgcga gaaatggttc agaaaaggga cagtcgtctt cgggaagcat acttgtcata   1440
cagaggtacc gaaaacaggg aagttatgga caacttactt aagatggcat taccaggaac   1500
cagttctggt ttgcacatcg ctcacatagc agcagagatg gctcctgtcg cgaaggttgg   1560
tggcctggca gatgtgatat ctggtcttgg gaaggcactt cagaaaaaag gccatctagt   1620
agagatcatt cttcccaaat acgactgcat gcaggttgac caagttagca atctaaaggt   1680
tttagatgtt cttgtgcagt cctactttga aggaaatatg ttcaacaaca aaatttggac   1740
cgggactgtt gaaggcctac ccgtgtactt tattgagcca cagcatccag cgatgttctt   1800
ttcgagggct cagtactatg gagagcatga tgacttcaaa cgttttttcat acttcagccg   1860 tgcggcacta gaattacttt atcaatctgg gaagaaagtt gatataatcc actgccatga   1920
ctggcaaact gcatttgttg cacctcttta ttgggatgta tatgcaaatc taggcttcaa   1980
ctcagctaga atttgcttca cctgtcataa ttttgaatac caaggaactg ctccagctcg   2040
tgatttagca tggtgtggtc ttgatgttga gcacctagac agaccagaca ggatgcggga   2100
caattcgcat ggcagaataa atgctgttaa gggagcagtt gtgtattcaa acatcgtgac   2160
aactgtctcg ccaacatatg cactagaggt tcgctcagag ggtgggcgtg gactccaaga   2220
tacacttaaa gtacattcca ggaaatttct tgggatactt aatggaatcg acacagatac   2280
atggaaccct tgcacagata ggtatctcaa ggtccagtat aatgctaagg atctccaggg   2340
aaaggcagcc aacaaagcag ccctcagaga gcaactaaac ctggcttctg catatccttc   2400
acaaccactg gttggttgca ttaccaggct ggttgctcag aagggtgtac atcttatcag   2460
gcatgcaata tacaaaacag ctgaattagg aggacagttt gtccttctgg gttcaagtcc   2520
agtaccagaa attcagaggg agtttgaagg tattgcagac cattttcaga acaacaacaa   2580
tatccggctg attttgaagt atgatgatgc gctgtctcat tgcatatatg ctgcgtctga   2640
catgttcatt gttccctcta tatttgagcc atgtggcctc actcagatga tagccatgag   2700
atatggttct gtgccaatcg ttcggaaaac tggtgggctg aatgacagtg tctttgactt   2760
cgatgacgaa acaatacccca tggaggtgcg gaacggcttt acatttgtca aggccgacga   2820
gcagggccta agcagcgcga tggagagggc gttcaactgc tacacgagga agcccgaggt   2880
gtggaaacag cttgtgcaga aagacatgac gatcgatttc agctgggaca cctcggcttc   2940
gcagtacgag gacatctacc agaaggcggt ggctcgagcg agggcagtgg cgtgagcaca   3000
cacacacacg gtagttggtt ccctgatgcc tctctcccct gccctgccct catgatacaa   3060
acggcactgg acgaaatcga gggatcatgg aaacagaatc atatagcaag ctccatgctc   3120
tcggcgcgca tttccggtaa gggtgtgacg gtgtatcgct ggttatatgc gctgtttatt   3180
gaaggcagaa cgcgagctaa aaatggagta gctaccgtga accctcaaga tcgtagtatg   3240
cgcgctgttg ttggcataat attggtgtaa attgtagtag gctgtatatt ttcttgaggg   3300
gttgcaacgg agctgtatgc gtgcagtgca ggctgcagag tcgcacgtat gtactgtatt   3360
```
atgcagaaaa aaaaaaaaaa aaaaaa                                              3386

<210> SEQ ID NO 12
<211> LENGTH: 914
<212> TYPE: PRT
<213> ORGANISM: Triticum aestivum

<400> SEQUENCE: 12

Met Ala Cys Ser Ala Ala Gly Val Glu Ala Thr Ala Leu Leu Ser
 1               5                  10                  15

Pro Arg Cys Pro Ala Pro Ser Pro Pro Asp Gly Arg Ser Arg Arg
                20                  25                  30

Leu Ala Leu Ala Ser Arg Thr Arg His Arg Ser Leu Arg Ala Ala Ala
                35                  40                  45

Gln Arg Pro His Lys Ser Ala Thr Gly Ala Asp Pro Leu Tyr Asn Asn
         50                  55                  60

Arg Ala Asn Val Arg Ser Asp Glu Ala Ser Val Ser Ala Glu Lys Glu
 65                  70                  75                  80

Arg Gln Arg Lys Tyr Asn Asp Gly Asp Gly Ile Ser Asn Leu Lys Leu
                 85                  90                  95

Glu Asp Leu Val Gly Met Ile Gln Asn Thr Glu Lys Asn Ile Leu Leu
                100                 105                 110

Leu Asn Gln Ala Arg Leu Gln Ala Met Glu His Ala Asp Lys Val Leu
            115                 120                 125

Lys Glu Lys Glu Ala Leu Gln Arg Lys Ile Asn Ile Leu Glu Thr Arg
130                 135                 140

Leu Ser Glu Thr Asp Glu Gln His Lys Leu Ser Ser Glu Gly Asn Phe
145                 150                 155                 160

Ser Asp Ser Pro Leu Ala Leu Glu Leu Gly Ile Leu Lys Glu Glu Asn
                165                 170                 175

Ile Leu Leu Lys Glu Asp Ile Glu Phe Phe Lys Thr Lys Leu Ile Glu
                180                 185                 190

Val Ala Glu Ile Glu Glu Gly Ile Phe Lys Leu Glu Lys Glu His Ala
            195                 200                 205

Leu Leu Asp Ala Ser Leu Arg Glu Leu Glu Ser Arg Phe Ile Ala Ala
210                 215                 220

Gln Ala Asp Thr Met Lys Leu Gly Pro Arg Asp Ala Trp Trp Glu Lys
225                 230                 235                 240

Val Glu Lys Leu Glu Asp Leu Leu Glu Thr Thr Ala Asn Gln Val Glu
                245                 250                 255

His Ala Ala Val Ile Leu Asp His Asn His Asp Leu Gln Asp Arg Leu
                260                 265                 270

Asp Asn Leu Glu Ala Ser Leu Gln Ala Ala Asn Ile Ser Lys Phe Ser
            275                 280                 285

Cys Ser Leu Val Asp Leu Leu Gln Gln Lys Val Lys Leu Val Glu Asp
        290                 295                 300

Arg Phe Gln Ala Cys Asn Ser Glu Met His Ser Gln Ile Glu Leu Tyr
305                 310                 315                 320

Glu His Ser Ile Val Glu Phe His Asp Thr Leu Ser Lys Leu Ile Glu
                325                 330                 335

Glu Ser Glu Lys Arg Ser Leu Glu Asn Phe Thr Gly Asn Met Pro Ser
            340                 345                 350

Glu Leu Trp Ser Lys Ile Ser Leu Leu Ile Asp Gly Trp Leu Leu Glu
        355                 360                 365

-continued

```
Lys Lys Ile Ser Tyr Asn Asp Ala Ser Met Leu Arg Glu Met Val Gln
    370                 375                 380
Lys Arg Asp Ser Arg Leu Arg Glu Ala Tyr Leu Ser Tyr Arg Gly Thr
385                 390                 395                 400
Glu Asn Arg Glu Val Met Asp Asn Leu Leu Lys Met Ala Leu Pro Gly
                405                 410                 415
Thr Ser Ser Gly Leu His Ile Ala His Ile Ala Ala Glu Met Ala Pro
            420                 425                 430
Val Ala Lys Val Gly Gly Leu Ala Asp Val Ile Ser Gly Leu Gly Lys
        435                 440                 445
Ala Leu Gln Lys Lys Gly His Leu Val Glu Ile Ile Leu Pro Lys Tyr
    450                 455                 460
Asp Cys Met Gln Val Asp Gln Val Ser Asn Leu Lys Val Leu Asp Val
465                 470                 475                 480
Leu Val Gln Ser Tyr Phe Glu Gly Asn Met Phe Asn Asn Lys Ile Trp
                485                 490                 495
Thr Gly Thr Val Glu Gly Leu Pro Val Tyr Phe Ile Glu Pro Gln His
            500                 505                 510
Pro Ala Met Phe Phe Ser Arg Ala Gln Tyr Tyr Gly Glu His Asp Asp
        515                 520                 525
Phe Lys Arg Phe Ser Tyr Phe Ser Arg Ala Ala Leu Glu Leu Leu Tyr
    530                 535                 540
Gln Ser Gly Lys Lys Val Asp Ile Ile His Cys His Asp Trp Gln Thr
545                 550                 555                 560
Ala Phe Val Ala Pro Leu Tyr Trp Asp Val Tyr Ala Asn Leu Gly Phe
                565                 570                 575
Asn Ser Ala Arg Ile Cys Phe Thr Cys His Asn Phe Glu Tyr Gln Gly
            580                 585                 590
Thr Ala Pro Ala Arg Asp Leu Ala Trp Cys Gly Leu Asp Val Glu His
        595                 600                 605
Leu Asp Arg Pro Asp Arg Met Arg Asp Asn Ser His Gly Arg Ile Asn
    610                 615                 620
Ala Val Lys Gly Ala Val Val Tyr Ser Asn Ile Val Thr Thr Val Ser
625                 630                 635                 640
Pro Thr Tyr Ala Leu Glu Val Arg Ser Glu Gly Gly Arg Gly Leu Gln
                645                 650                 655
Asp Thr Leu Lys Val His Ser Arg Lys Phe Leu Gly Ile Leu Asn Gly
            660                 665                 670
Ile Asp Thr Asp Thr Trp Asn Pro Cys Thr Asp Arg Tyr Leu Lys Val
        675                 680                 685
Gln Tyr Asn Ala Lys Asp Leu Gln Gly Lys Ala Ala Asn Lys Ala Ala
    690                 695                 700
Leu Arg Glu Gln Leu Asn Leu Ala Ser Ala Tyr Pro Ser Gln Pro Leu
705                 710                 715                 720
Val Gly Cys Ile Thr Arg Leu Val Ala Gln Lys Gly Val His Leu Ile
                725                 730                 735
Arg His Ala Ile Tyr Lys Thr Ala Glu Leu Gly Gly Gln Phe Val Leu
            740                 745                 750
Leu Gly Ser Ser Pro Val Pro Glu Ile Gln Arg Glu Phe Glu Gly Ile
        755                 760                 765
Ala Asp His Phe Gln Asn Asn Asn Ile Arg Leu Ile Leu Lys Tyr
    770                 775                 780
```

```
Asp Asp Ala Leu Ser His Cys Ile Tyr Ala Ala Ser Asp Met Phe Ile
785                 790                 795                 800

Val Pro Ser Ile Phe Glu Pro Cys Gly Leu Thr Gln Met Ile Ala Met
                805                 810                 815

Arg Tyr Gly Ser Val Pro Ile Val Arg Lys Thr Gly Gly Leu Asn Asp
            820                 825                 830

Ser Val Phe Asp Phe Asp Asp Glu Thr Ile Pro Met Glu Val Arg Asn
        835                 840                 845

Gly Phe Thr Phe Val Lys Ala Asp Glu Gln Gly Leu Ser Ser Ala Met
    850                 855                 860

Glu Arg Ala Phe Asn Cys Tyr Thr Arg Lys Pro Glu Val Trp Lys Gln
865                 870                 875                 880

Leu Val Gln Lys Asp Met Thr Ile Asp Phe Ser Trp Asp Thr Ser Ala
                885                 890                 895

Ser Gln Tyr Glu Asp Ile Tyr Gln Lys Ala Val Ala Arg Ala Arg Ala
            900                 905                 910

Val Ala

<210> SEQ ID NO 13
<211> LENGTH: 874
<212> TYPE: PRT
<213> ORGANISM: Vigna unguiculata

<400> SEQUENCE: 13

Met Ile Lys Asn Ala Glu Lys Asn Ile Leu Leu Asn Gln Ala Arg
1               5                   10                  15

Val His Ala Leu Glu Asp Leu Glu Lys Ile Leu Ala Glu Lys Glu Ala
                20                  25                  30

Leu Gln Gly Glu Ile Asn Val Leu Ala Met Arg Leu Ala Glu Ser Asp
            35                  40                  45

Val Arg Ile Glu Val Ala Ala Gln Glu Lys Thr Arg Val Glu Leu Leu
        50                  55                  60

Glu Gly Glu Leu Glu Lys Leu Arg Ser Glu Leu Ala Gln Lys Gly Ser
65                  70                  75                  80

Ile Glu Gly Arg Asp Ala Glu Leu His Glu Leu Gln Asn Gly Val Phe
                85                  90                  95

Ser Asp Ala Ile Thr Asn Asn Leu Ser His Asn Asp Lys Ile His Ser
            100                 105                 110

Leu Thr Glu Glu Leu Asn Ser Ile Arg Glu Glu Asn Ala Thr Leu Lys
        115                 120                 125

Asn Ala Ile Glu Ser Phe Lys Ala Gln Leu Asn Asp Val Ala Asn Asn
130                 135                 140

Asp Glu Arg Leu Ala Val Leu Glu Lys Glu Arg Leu Ser Leu Arg Ser
145                 150                 155                 160

Ala Leu Lys Asp Met Glu Ser Lys Leu Ser Ile Phe Pro Glu Asp Val
                165                 170                 175

Ser Glu Leu Ser Thr Leu Arg Val Glu Cys Lys Asp Leu Ser Asp Lys
            180                 185                 190

Val Glu Asn Leu Gln Leu Leu Asp Lys Ala Thr Lys Gln Asp Ser
        195                 200                 205

Gln Ala Val Thr Val Leu Gln Gln Asn Gln Asp Leu Gln Arg Lys Val
    210                 215                 220

Asp Lys Leu Glu Ala Ser Leu Glu Glu Ala Asn Ile Tyr Lys Leu Ser
225                 230                 235                 240
```

-continued

```
Ser Asp Lys Leu Gln Lys Ser Asn Glu Leu Met Gln Lys Ile Lys
            245                 250                 255
Leu Leu Glu Ser Gln Leu Gln Lys Ser Asp Glu Asp Ile Asn Ser Tyr
            260                 265                 270
Val Gln Leu Tyr Gln Gln Ser Val Lys Glu Phe Gln Asp Thr Leu Asp
            275                 280                 285
Leu Leu Lys Lys Glu Ser Lys Arg Arg Ala Pro Asp Glu Pro Val Glu
    290                 295                 300
Asp Met Pro Trp Glu Phe Trp Ser Arg Leu Leu Leu Ile Asp Gly
305                 310                 315                 320
Trp Ala Leu Glu Lys Lys Ile Ser Val Asp Asp Ala Lys Leu Leu Arg
                325                 330                 335
Glu Lys Val Trp Lys Arg Asp Lys Ser Val Ser Asp Val Tyr Met Ala
            340                 345                 350
Tyr Lys Glu Lys Thr Glu His Glu Ala Ile Ser Ala Phe Leu Gly Leu
        355                 360                 365
Thr Ser Ser Ala Thr Ser Pro Gly Leu Tyr Val Ile His Ile Ala Ala
    370                 375                 380
Glu Met Ala Pro Val Ala Lys Val Gly Gly Leu Gly Asp Val Ile Ser
385                 390                 395                 400
Gly Leu Ser Lys Ala Leu Gln Lys Lys Gly His Leu Val Glu Ile Ile
                405                 410                 415
Leu Pro Lys Tyr Asp Cys Met Gln Tyr Asp Arg Ile Gly Asp Leu Arg
            420                 425                 430
Ala Leu Asp Val Val Ile Glu Ser Tyr Phe Asp Gly Gln Leu Phe Lys
        435                 440                 445
Asn Lys Ile Trp Val Gly Thr Val Glu Gly Leu Pro Val Tyr Phe Ile
    450                 455                 460
Glu Pro His His Pro Gly Lys Phe Phe Trp Arg Gly Asp Tyr Tyr Gly
465                 470                 475                 480
Ala His Asp Asp Phe Arg Arg Phe Ser Tyr Phe Ser Arg Ala Ala Leu
                485                 490                 495
Glu Phe Leu Leu Gln Ala Gly Lys Lys Pro Asp Ile Ile His Cys His
            500                 505                 510
Asp Trp Gln Thr Ala Phe Ile Ala Pro Leu Tyr Trp Asp Val Tyr Ala
        515                 520                 525
Pro Lys Gly Leu Asn Ser Ala Arg Ile Cys Phe Thr Cys His Asn Phe
    530                 535                 540
Glu Tyr Gln Gly Thr Ala Gly Ala Ser Glu Leu Glu Ala Cys Gly Leu
545                 550                 555                 560
Asp Ser His Gln Leu Asn Arg Pro Asp Arg Met Gln Asp Asn Ser Ala
                565                 570                 575
His Asn Arg Val Asn Ser Val Lys Gly Ala Val Val Tyr Ser Asn Ile
            580                 585                 590
Val Thr Thr Val Ser Pro Thr Tyr Ala Gln Glu Val Arg Thr Ala Glu
        595                 600                 605
Gly Gly Lys Gly Leu His Ser Thr Leu Ser Thr His Ser Lys Lys Phe
    610                 615                 620
Ile Gly Ile Leu Asn Gly Ile Asp Thr Asp Ile Trp Asn Pro Ala Thr
625                 630                 635                 640
Asp Pro Phe Leu Gln Val Gln Tyr Asn Ala Asn Asp Leu Gln Gly Lys
                645                 650                 655
Ser Glu Asn Lys Glu Ala Leu Arg Arg Asn Leu Gly Leu Ser Ser Ala
```

```
                660                  665                  670
Asp Val Arg Arg Pro Leu Val Gly Cys Ile Thr Arg Leu Val Pro Gln
        675                  680                  685
Lys Gly Val His Leu Ile Arg His Ala Ile Tyr Leu Thr Leu Glu Leu
        690                  695                  700
Gly Gly Gln Phe Val Leu Leu Gly Ser Ser Pro Val Pro His Ile Gln
705                  710                  715                  720
Arg Glu Phe Glu Gly Ile Ala Asn His Phe Gln Asn His Asp His Ile
                725                  730                  735
Arg Leu Ile Leu Lys Tyr Asp Glu Ser Leu Ser His Ala Ile Tyr Ala
            740                  745                  750
Ala Ser Asp Met Phe Ile Ile Pro Ser Ile Phe Glu Pro Cys Gly Leu
        755                  760                  765
Thr Gln Met Ile Ser Met Arg Tyr Gly Ala Ile Pro Ile Ala Arg Lys
        770                  775                  780
Thr Gly Gly Leu Asn Asp Ser Val Phe Asp Val Asp Asp Thr Ile
785                  790                  795                  800
Pro Ser Gln Phe Arg Asn Gly Phe Thr Phe Leu Asn Ala Asp Glu Lys
                805                  810                  815
Gly Ile Asn Asp Ala Leu Val Arg Ala Ile Asn Leu Phe Thr Asn Asp
                820                  825                  830
Pro Lys Ser Trp Lys Gln Leu Val Gln Lys Asp Met Asn Ile Asp Phe
            835                  840                  845
Ser Trp Asp Ser Ser Ala Ala Gln Tyr Glu Glu Leu Tyr Ser Lys Ser
    850                  855                  860
Val Thr Arg Gly Arg Ala Thr Lys Arg Ala
865                  870
```